United States Patent
Ogo et al.

(10) Patent No.: US 9,522,824 B2
(45) Date of Patent: Dec. 20, 2016

(54) METAL COMPLEX AND METHOD FOR PRODUCING HYDROGEN PEROXIDE

(71) Applicants: MITSUBISHI GAS CHEMICAL COMPANY, INC., Chiyoda-ku (JP); KYUSHU UNIVERSITY, NATIONAL UNIVERSITY CORPORATION, Fukuoka-shi (JP)

(72) Inventors: Seiji Ogo, Fukuoka (JP); Kenji Kato, Chiyoda-ku (JP); Masaki Nagata, Chiyoda-ku (JP)

(73) Assignees: MITSUBISHI GAS CHEMICAL COMPANY, INC., Chiyoda-ku (JP); KYUSHU UNIVERSITY, NATIONAL UNIVERSITY CORPORATION, Fukuoka-shi (JP)

( * ) Notice: Subject to any disclaimer, the term of this patent is extended or adjusted under 35 U.S.C. 154(b) by 0 days.

(21) Appl. No.: 14/429,104

(22) PCT Filed: Aug. 2, 2013

(86) PCT No.: PCT/JP2013/071015
§ 371 (c)(1),
(2) Date: Mar. 18, 2015

(87) PCT Pub. No.: WO2014/045732
PCT Pub. Date: Mar. 27, 2014

(65) Prior Publication Data
US 2015/0225236 A1    Aug. 13, 2015

(30) Foreign Application Priority Data

Sep. 19, 2012  (JP) ................................ 2012-205229

(51) Int. Cl.
*B01J 21/18*   (2006.01)
*B01J 23/38*   (2006.01)
(Continued)

(52) U.S. Cl.
CPC .............. *C01B 15/029* (2013.01); *B01J 31/22* (2013.01); *B01J 31/2295* (2013.01);
(Continued)

(58) Field of Classification Search
None
See application file for complete search history.

(56) References Cited

U.S. PATENT DOCUMENTS 5,149,880 A   9/1992  Sawyer et al.
6,168,775 B1  1/2001  Zhou et al.
(Continued)

FOREIGN PATENT DOCUMENTS

JP    40-19006 B2   8/1965
JP    57-246 B2     1/1982
(Continued)

OTHER PUBLICATIONS

Extended Search Report issued Feb. 23, 2016 in European Patent Application No. 13839234.5.
Riccardo F. Carina, et al., "Modulation of iron reduction potential by deprotonation at a remote site", Chemical Communications—CHEMCOM , No. 24, 1998, XP055246540, pp. 2681-2682.
International Search Report issued Nov. 5, 2013 in PCT/JP2013/071015.
Brian G. Hashiguchi, et al., "Acceleration of Nucleophilic CH Activation by Strongly Basic Solvents" Journal of the American Chemical Society, vol. 132, No. 36, 2010, pp. 12542-12545.
Chi-Ming Che, et al., "Single microcrystals of organoplatinum (II) complexes with high charge-carrier mobility" Chemical Science, vol. 2, No. 2, 2011, pp. 216-220.
(Continued)

*Primary Examiner* — Yun Qian
(74) *Attorney, Agent, or Firm* — Oblon, McClelland, Maier & Neustadt, L.L.P.

(57) ABSTRACT

An object of the present invention is to provide a novel method for producing hydrogen peroxide by direct synthesis that is capable of taking the place of the conventional anthraquinone process, and to provide a catalyst used in the production method.
The present invention is a metal complex represented by the following general formula (1), (2), (3) or (4).

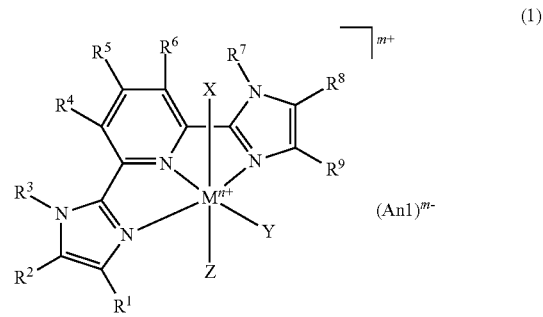

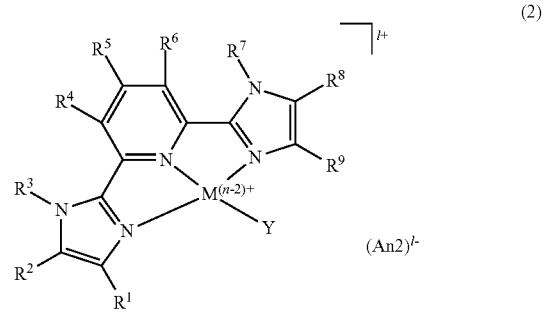

(Continued)

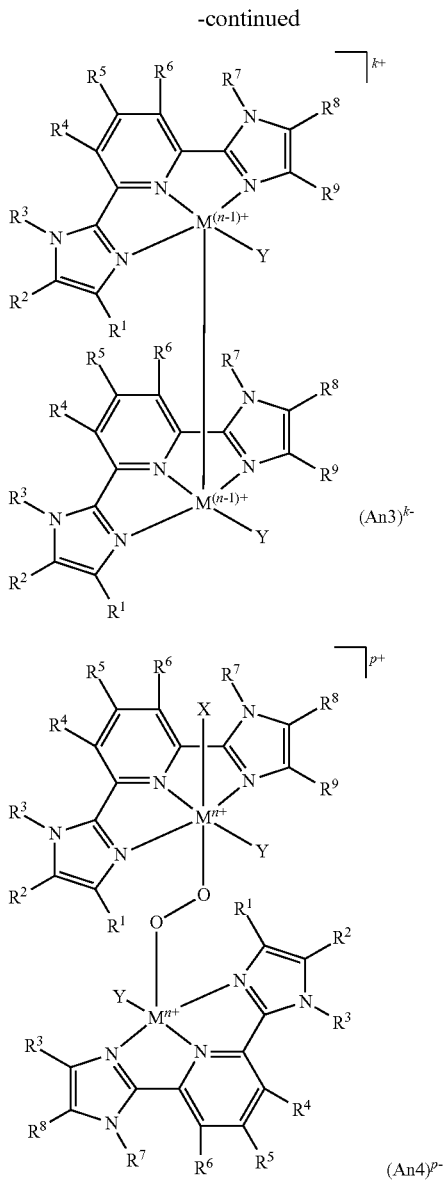

(51) Int. Cl.
*B01J 23/40* (2006.01)
*C01B 15/029* (2006.01)
*C07D 401/14* (2006.01)
*C07F 11/00* (2006.01)
*C07F 13/00* (2006.01)
*C07F 15/00* (2006.01)
*C07F 15/02* (2006.01)
*C07F 15/04* (2006.01)
*C07F 15/06* (2006.01)
*C07F 1/00* (2006.01)
*B01J 31/22* (2006.01)
*C01B 15/022* (2006.01)
*C07F 1/08* (2006.01)
*C07F 1/10* (2006.01)
*C07F 1/12* (2006.01)
*C07F 19/00* (2006.01)
*B01J 31/18* (2006.01)

(52) U.S. Cl.
CPC .......... *C01B 15/022* (2013.01); *C07D 401/14* (2013.01); *C07F 1/005* (2013.01); *C07F 1/08* (2013.01); *C07F 1/10* (2013.01); *C07F 1/12* (2013.01); *C07F 11/00* (2013.01); *C07F 11/005* (2013.01); *C07F 13/00* (2013.01); *C07F 13/005* (2013.01); *C07F 15/00* (2013.01); *C07F 15/004* (2013.01); *C07F 15/008* (2013.01); *C07F 15/0026* (2013.01); *C07F 15/0053* (2013.01); *C07F 15/0066* (2013.01); *C07F 15/0093* (2013.01); *C07F 15/02* (2013.01); *C07F 15/025* (2013.01); *C07F 15/04* (2013.01); *C07F 15/045* (2013.01); *C07F 15/06* (2013.01); *C07F 15/065* (2013.01); *C07F 19/00* (2013.01); *B01J 31/1815* (2013.01); *B01J 2231/005* (2013.01); *B01J 2531/16* (2013.01); *B01J 2531/17* (2013.01); *B01J 2531/18* (2013.01); *B01J 2531/62* (2013.01); *B01J 2531/64* (2013.01); *B01J 2531/66* (2013.01); *B01J 2531/72* (2013.01); *B01J 2531/74* (2013.01); *B01J 2531/821* (2013.01); *B01J 2531/822* (2013.01); *B01J 2531/824* (2013.01); *B01J 2531/825* (2013.01); *B01J 2531/827* (2013.01); *B01J 2531/828* (2013.01); *B01J 2531/842* (2013.01); *B01J 2531/845* (2013.01); *B01J 2531/847* (2013.01)

(56) References Cited

U.S. PATENT DOCUMENTS 6,274,114 B1 8/2001 Ledon et al.
2007/0219074 A1 9/2007 Pride

FOREIGN PATENT DOCUMENTS

JP 57-47304 A 3/1982
JP 2009-530503 A 8/2009

OTHER PUBLICATIONS

Jennifer K. Edwards, et al., "Switching Off Hydrogen Peroxide Hydrogenation in the Direct Synthesis Process" Science, vol. 323, 2009, pp. 1037-1041.
Notification of Reasons for Refusal issued by the JPO on Jul. 14, 2016, in Patent Application No. 2012-205229 with English translation.

2 Claims, No Drawings

METAL COMPLEX AND METHOD FOR PRODUCING HYDROGEN PEROXIDE

CROSS REFERENCE TO RELATED APPLICATIONS

The present application is a 35 U.S.C. §371 national stage patent application of International patent application PCT/JP2013/071015, filed on Aug. 2, 2013, published as WO/2014/045732 on Mar. 27, 2014, the text of which is incorporated by reference, and claims the benefit of the filing date of Japanese application no. 2012-205229, filed on Sep. 19, 2012, the text of which is also incorporated by reference.

TECHNICAL FIELD

The present invention relates to a metal complex that is useful as a catalyst for direct synthesis of hydrogen peroxide and a method for producing hydrogen peroxide that uses that metal complex. The metal complex enables stepwise control of the reactions at each stage, from a reaction that extracts electrons from hydrogen to the formation of hydrogen peroxide, by functioning as a catalyst of a homogeneous system.

BACKGROUND ART

Hydrogen peroxide has an oxidizing power such that it exhibits strong bleaching and germicidal actions. Therefore, hydrogen peroxide is utilized as a bleaching agent for, for example, paper, pulp, and fibers, or as a germicide. Further, hydrogen peroxide is an important industrial product widely used in oxidation reactions including epoxidation and hydroxylation.

Further, hydrogen peroxide is used in the semiconductor industry, specifically used in, for example, cleaning of the surfaces of semiconductor substrates and the like, chemical polishing of the surfaces of copper, tin, and other copper alloys, and etching for electronic circuit. Hydrogen peroxide produces only water and oxygen as decomposition products, and hence is considered important from the viewpoint of green chemistry, and has attracted attention as a substitute material for a chlorine bleaching agent.

Although hydrogen peroxide is currently synthesized industrially by an anthraquinone process, since this process consumes a large amount of energy, there is a need to develop a new synthesis method.

As one alternative method, there has been considerable activity in the development of a method for synthesizing hydrogen peroxide directly from hydrogen and oxygen. Non-homogeneous solid catalysts have typically been developed for use as catalysts of this direct synthesis method, and various non-homogeneous solid catalysts have been reported. For example, Patent Document 1 and Non-Patent Document 1 disclose that hydrogen peroxide is synthesized directly from hydrogen and oxygen using an alloy solid catalyst such as platinum-palladium.

In addition, organometallic complexes, in which various ligands are used for the metal elements such as members of the platinum group or iron group, have also been proposed for use as catalysts for direct synthesis of hydrogen peroxide (Patent Documents 2 and 3).

PRIOR ART DOCUMENTS

Patent Documents

Patent Document 1: Japanese Examined Patent Publication No. S40-19006

Patent Document 2: Japanese Examined Patent Publication No. S57-246

Patent Document 3: Japanese Laid Open Patent Publication (kohyo) No. 2009-530503

Non-Patent Documents

Non-Patent Document 1: Edwards, J. K., et al., Science, Vol. 323, p. 1037, 2009

DISCLOSURE OF THE INVENTION

Problems to be Solved by the Invention

An object of the present invention is to provide a novel method for producing hydrogen peroxide by direct synthesis that is capable of taking the place of the conventional anthraquinone process, and to provide a catalyst used in the production method.

Means for Solving the Problems

As a result of conducting extensive studies in consideration of the aforementioned problems, the inventors of the present invention have found that a metal complex represented by the general formula (1) below returns to the metal complex of general formula (1) after going through the stepwise formation of metal complexes represented by the general formulas (2) to (4) below by introducing hydrogen and oxygen, that the extraction of electrons from hydrogen, the donation of electrons to oxygen, and the formation of hydrogen peroxide occur, and that these reactions can be easily controlled in a stepwise manner, thereby leading to completion of the present invention.

Namely, the present invention is as described below.

[1] A metal complex represented by the following general formula (1), (2), (3) or (4):

[Chemical Formula 1]

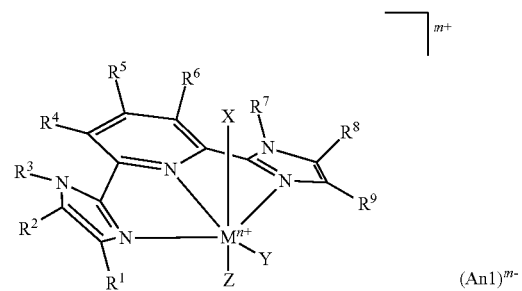

(1)

[wherein, M represents chromium, manganese, iron, cobalt, nickel, copper, molybdenum, ruthenium, rhodium, palladium, silver, tungsten, rhenium, osmium, iridium, platinum or gold, n+ represents the charge of M, $R^1$, $R^2$, $R^3$, $R^4$, $R^5$, $R^6$, $R^7$, $R^8$ and $R^9$ each independently represent a hydrogen atom, halogen, hydroxyl group, alkyl group having 1 to 20 carbon atoms, aralkyl group having 7 to 20 carbon atoms, aryl group having 6 to 20 carbon atoms, silyl group substituted with a hydrocarbon group having 1 to 20 carbon atoms, alkoxy group having 1 to 20 carbon atoms, aralkyloxy group having 7 to 20 carbon atoms, aryloxy group having 6 to 20 carbon atoms or amino group substituted with a hydrocarbon group having 1 to 20 carbon atoms, X, Y and Z each independently represent H₂O, OH⁻, O²⁻ or a halogen ion, m+ represents the charge of the moiety of the metal complex excluding An1, An1 represents a counter ion that neutralizes the charge of the moiety of the metal complex excluding An1, m− represents the charge of An1, and the alkyl group, aralkyl group, aryl group, silyl group, alkoxy group, aralkyloxy group, aryloxy group and amino group may be substituted with a hydroxyalkoxyalkoxy group];

[Chemical Formula 2]

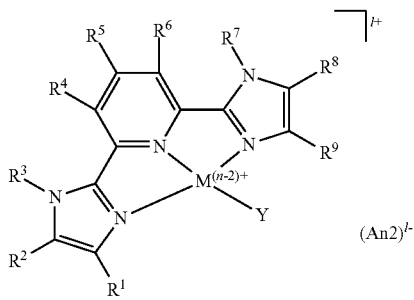

(2)

[wherein, M, n, $R^1$ to $R^9$ and Y are the same as defined in formula (1), 1+ represents the charge of the moiety of the metal complex excluding An2, An2 represents a counter ion that neutralizes the charge of the moiety of the metal complex excluding An2, and 1−represents the charge of An2];

[Chemical Formula 3]

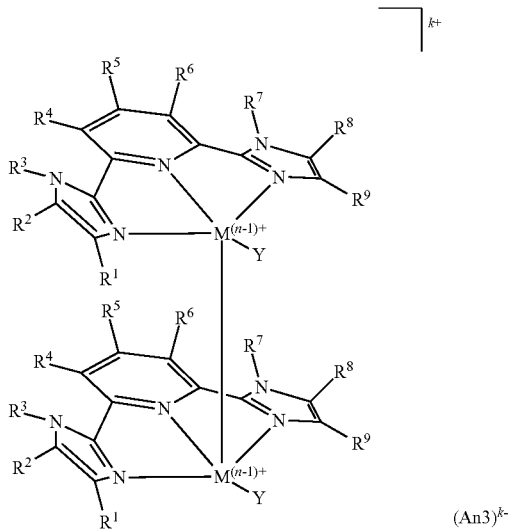

(3)

[wherein, M, n, $R^1$ to $R^9$ and Y are the same as defined in formula (1), k+ represents the charge of the moiety of the metal complex excluding An3, An3 represents a counter ion that neutralizes the charge of the moiety of the metal complex excluding An3, k− represents the charge of An3, and two each of the M, n, $R^1$ to $R^9$ and Y may each be the same or different]; and,

[Chemical Formula 4]

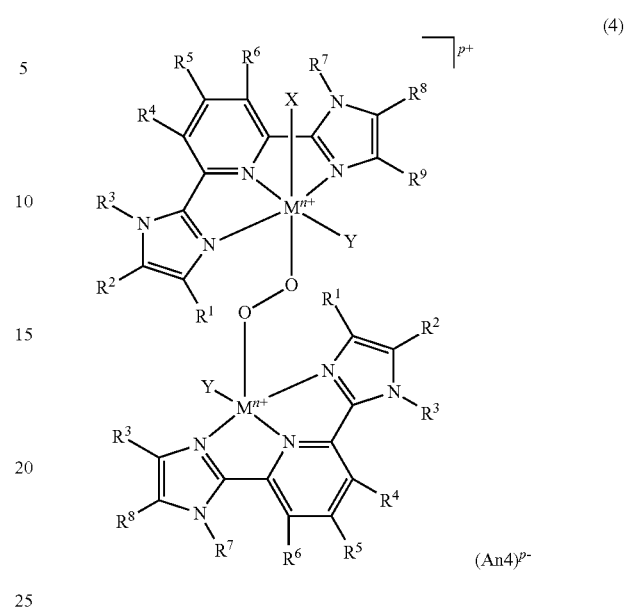

(4)

[wherein, M, n, $R^1$ to $R^9$, X and Y are the same as defined in formula (1), p+ represents the charge of the moiety of the metal complex excluding An4, An4 represents a counter ion that neutralizes the charge of the moiety of the metal complex excluding An4, p− represents the charge of An4, and two each of the M, n, $R^1$ to $R^9$, X and Y may each be the same or different].

[2] The metal complex described in [1], wherein the number of carbon atoms of the alkyl group is 1 to 4, the number of carbon atoms of the aralkyl group is 7 to 10, the number of carbon atoms of the aryl group is 6 to 9, the number of carbon atoms of the alkoxy group is 1 to 4, the number of carbon atoms of the aralkyloxy group is 7 to 10, and the number of carbon atoms of the aryloxy group is 6 to 9.

[3] The metal complex described in [1] or [2], wherein, in general formula (1), $R^1$, $R^2$, $R^4$, $R^5$, $R^6$, $R^8$ and $R^9$ represent hydrogen atoms, $R^3$ and $R^7$ represent methyl groups, one of X, Y and Z represents OH⁻, the remaining two represent H₂O, and An1 represents a nitrate ion.

[4] The metal complex described in [1] or [2], wherein, in general formula (2), $R^1$, $R^2$, $R^4$, $R^5$, $R^6$, $R^8$ and $R^9$ represent hydrogen atoms, $R^3$ and $R^7$ represent methyl groups, Y represents H₂O and An2 represents a nitrate ion.

[5] The metal complex described in [1] or [2], wherein, in general formula (3), $R^1$, $R^2$, $R^4$, $R^5$, $R^6$, $R^8$ and $R^9$ represent hydrogen atoms, $R^3$ and $R^7$ represent methyl groups, Y represents H₂O and An3 represents a nitrate ion.

[6] The metal complex described in [1] or [2], wherein, in general formula (4), $R^1$, $R^2$, $R^4$, $R^5$, $R^6$, $R^8$ and $R^9$ represent hydrogen atoms, $R^3$ and $R^7$ represent methyl groups, X and Y represent H₂O and An4 represents a nitrate ion.

[7] A method for producing hydrogen peroxide comprising the formation of hydrogen peroxide from hydrogen and oxygen in the presence of a metal complex represented by the following general formula (1):

[Chemical Formula 5]

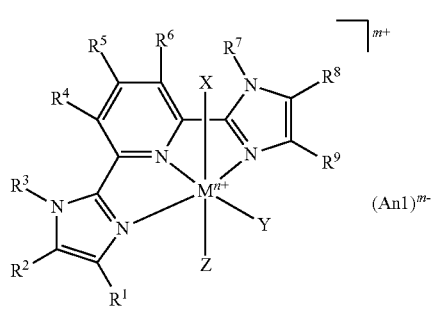

[wherein, M represents chromium, manganese, iron, cobalt, nickel, copper, molybdenum, ruthenium, rhodium, palladium, silver, tungsten, rhenium, osmium, iridium, platinum or gold, n+ represents the charge of M, $R^1$, $R^2$, $R^3$, $R^4$, $R^5$, $R^6$, $R^7$, $R^8$ and $R^9$ each independently represent a hydrogen atom, halogen, hydroxyl group, alkyl group having 1 to 20 carbon atoms, aralkyl group having 7 to 20 carbon atoms, aryl group having 6 to 20 carbon atoms, silyl group substituted with a hydrocarbon group having 1 to 20 carbon atoms, alkoxy group having 1 to 20 carbon atoms, aralkyloxy group having 7 to 20 carbon atoms, aryloxy group having 6 to 20 carbon atoms or amino group substituted with a hydrocarbon group having 1 to 20 carbon atoms, X, Y and Z each independently represent $H_2O$, $OH^-$, $O^{2-}$ or a halogen ion, m+ represents the charge of the moiety of the metal complex excluding An1, An1 represents a counter ion that neutralizes the charge of the moiety of the metal complex excluding An1, m− represents the charge of An1, and the alkyl group, aralkyl group, aryl group, silyl group, alkoxy group, aralkyloxy group, aryloxy group and amino group may be substituted with a hydroxyalkoxyalkoxy group].

Effects of the Invention

According to the present invention, a novel method for producing hydrogen peroxide by direct synthesis and a catalyst used in the production method are provided. In this production method, each reaction from the extraction of electrons from hydrogen to the formation of hydrogen peroxide can be easily controlled in a stepwise manner.

MODE FOR CARRYING OUT THE INVENTION

The following provides a detailed explanation of the present invention.

[Metal Complex]

The metal complex of the present invention is represented by the following general formula (1).

[Chemical Formula 6]

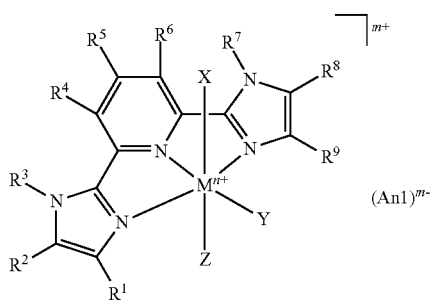

<M and n+>

In general formula (1), M represents chromium, manganese, iron, cobalt, nickel, copper, molybdenum, ruthenium, rhodium, palladium, silver, tungsten, rhenium, osmium, iridium, platinum or gold. Any of these metals can adopt any of the coordinate structures represented by general formulas (1) to (4), and function as the central metal in the metal complex of the present invention. In addition, n+ represents the charge of M and is a number within the range of +7 to 0.

M is preferably rhodium from the viewpoint of catalytic efficiency in the case of using the metal complex of the present invention for catalyzing the synthesis of hydrogen peroxide.

<$R^1$ to $R^9$>

In general formula (1), $R^1$, $R^2$, $R^3$, $R^4$, $R^5$, $R^6$, $R^7$, $R^8$ and $R^9$ each independently represent a hydrogen atom, halogen, hydroxyl group, alkyl group having 1 to 20 carbon atoms, aralkyl group having 7 to 20 carbon atoms, aryl group having 6 to 20 carbon atoms, silyl group substituted with a hydrocarbon group having 1 to 20 carbon atoms, alkoxy group having 1 to 20 carbon atoms, aralkyloxy group having 7 to 20 carbon atoms, aryloxy group having 6 to 20 carbon atoms or amino group substituted with a hydrocarbon group having 1 to 20 carbon atoms. The alkyl group, aralkyl group, aryl group, silyl group, alkoxy group, aralkyloxy group, aryloxy group and amino group may be substituted with a hydroxyalkoxyalkoxy group.

Examples of the aforementioned halogen include fluorine, chlorine, bromine and iodine. Among these, chlorine is preferable.

In addition, examples of hydrocarbon groups having 1 to 20 carbon atoms that substitute on the aforementioned silyl group include a methyl group, ethyl group, propyl group and butyl group. Since a silyl group is substituted with a maximum of three hydrocarbon groups, the maximum number of carbon atoms in a single hydrocarbon group-substituted silyl group is 60.

Examples of hydrocarbon groups having 1 to 20 carbon atoms that substitute on the aforementioned amino group are the same as the hydrocarbon groups that substitute on the aforementioned silyl group. Since an amino group is substituted with a maximum of two hydrocarbon groups, the maximum number of carbon atoms in a single hydrocarbon group-substituted amino group is 40.

Moreover, from the viewpoints of high reactivity in the case of using the metal complex of the present invention for the synthesis of hydrogen peroxide and availability of raw materials used to produce the aforementioned metal complex, the number of carbon atoms of the aforementioned alkyl group is preferably 1 to 4, the number of carbon atoms of the aforementioned aralkyl group is preferably 7 to 10, the number of carbon atoms of the aforementioned aryl group is preferably 6 to 9, the number of carbon atoms of the aforementioned alkoxy group is preferably 1 to 4, the number of carbon atoms of the aforementioned aralkyloxy group is preferably 7 to 10, and the number of carbon atoms of the aforementioned aryloxy group is preferably 6 to 9.

Specific examples of such alkyl groups include a methyl group, ethyl group, propyl group and butyl group.

Specific examples of aralkyl groups include a benzyl group and phenethyl group.

Specific examples of aryl groups include a phenyl group, tolyl group, xylyl group and mesityl group.

Specific examples of alkoxy groups include an ethoxy group, methoxy group, propoxy group and butoxy group.

Specific examples of aralkyloxy groups include a benzyloxy group and phenethyloxy group.

Specific examples of aryloxy groups include a phenyloxy group, tolyloxy group, xylyloxy group and mesityloxy group.

$R^1$ to $R^9$ are preferably such that $R^1$, $R^2$, $R^4$ to $R^6$, $R^8$ and $R^9$ are hydrogen atoms and $R^3$ and $R^7$ are hydrocarbon groups having 1 to 20 carbon atoms or hydrogen atoms, and more preferably such that $R^1$, $R^2$, $R^4$ to $R^6$, $R^8$ and $R^9$ are hydrogen atoms and $R^3$ and $R^7$ are methyl groups, from the viewpoint of high reactivity.

<X, Y and Z>

X, Y and Z in the aforementioned general formula (1) each independently represent $H_2O$, $OH^-$, $O^{2-}$ or a halogen ion. Examples of the halogen ion include a fluoride ion, chloride ion, bromide ion and iodide ion, and among these, a chloride ion is preferable.

X, Y and Z are coordinated with the metal M together with the N atoms on two imidazole rings and an N atom on a pyridine ring. Furthermore, the valence of M in general formula (1) is +3 and the metal in this form prefers hexa-coordination.

In the method for producing hydrogen peroxide of the present invention to be subsequently described, a structure in which an imidazole ring, pyridine ring and imidazole ring are coordinated with the metal M in this order in the metal complex of the present invention (see general formula (1)) is an important key structure. Moreover, since this ligand structure (key structure) is rigidly fixed by the coordination of X, Y and Z, substituents on the imidazole rings and pyridine ring have little effect on this key structure.

One of X, Y and Z is preferably $OH^-$ and the remaining two are preferably $H_2O$ from the viewpoint of high reactivity. Furthermore, although whether X, Y and Z are $H_2O$, $OH^-$ or $O^{2-}$ is largely dependent on the pH of the solution obtained by dissolving the metal complex of the present invention in a reaction medium to be subsequently described, and on the pH of the production system at the production stage of the metal complex of the present invention, X, Y and Z are each independently selected from the aforementioned $H_2O$, $OH^-$, $O^{2-}$ and a halogen ion in a combination such that the charge of the moiety of general formula (1) excluding An1 (to also be referred to as "moiety 1") is from 0 to +3.

<m+>

In the aforementioned general formula (1), m+ represents the charge of moiety 1, and can adopt a charge within the range of 0 to +3 according to the types of X, Y and Z.

<An1 and m−>

In the aforementioned general formula (1), An1 represents a counter ion used to make the overall charge of the metal complex 0 by neutralizing the charge of the moiety 1. The number of counter ions is the number required to neutralize the charge of the moiety 1. Thus, the overall charge of An1 is m−, and m− can adopt a charge within the range of −3 to 0. Furthermore, An1 is not present in the case m+ is 0, namely in the case m− is also 0.

Examples of the counter ion include nitrate ion, trifluoromethanesulfonate ion, sulfate ion, tetrafluoroborate ion, tetraphenylborate ion, hexafluorophosphate ion, chloride ion, bromide ion and iodide ion. The counter ion is preferably a nitrate ion or trifluoromethanesulfonate ion from the viewpoint of facilitating production of the metal complex of the present invention.

<Metal Complex of Present Invention>

Preferable examples of the metal complex of the present invention composed of the key structure and various substituents and the like as previously explained are as indicated below.

(1) Metal complex wherein, in general formula (1), $R^1$, $R^2$, $R^4$, $R^5$, $R^6$, $R^8$ and $R^9$ represent hydrogen atoms, $R^3$ and $R^7$ represent methyl groups, one of X, Y and Z represents $OH^-$, the remaining two represent $H_2O$, and An1 represents a nitrate ion.

(2) Metal complex wherein, in general formula (1), $R^3$ and $R^7$ independently represent a hydrogen atom or methyl group, $R^5$ represents a hydrogen atom, hydroxyl group or (2-(2-(2-hydroxyethoxyl)ethoxy)ethoxy group, and X, Y and Z each independently represent $H_2O$ or $OH^-$.

[Metal Complex Production Method]

The metal complex of the present invention as explained above can be produced in the manner indicated below.

First, a metal M capable of adopting a hexa-coordination in general formula (1) is provided. This is typically commercially available in the form of a halide, hydrate or oxide and the like. The metal complex of the present invention is obtained by mixing or heating to reflux the metal with a Compound 1, which is represented by the following formula and serves as a ligand in the metal complex of the present invention, in a suitable solvent such as ethanol.

[Chemical Formula 7]

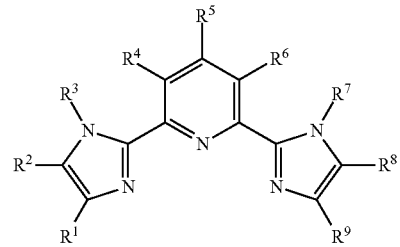

In the resulting metal complex of the present invention, if a halide has been used for the metal M, then X, Y and Z are halogen ions or solvent-derived ions thereof, and in the case the counter ion An1 is present, it is also a halogen ion or solvent-derived ion thereof.

The heating to reflux is normally carried out for 1 to 48 hours.

In addition, Compound 1 serving as the aforementioned ligand can be synthesized in accordance with the method described in R. F. Carina, G. Bernardinelli and A. F. Williams, Angew. Chem. Int. Ed., 1993, 32, 1463.

In addition, X, Y, Z and An1 can be altered by reacting an appropriate reagent and the like with the metal complex of the present invention synthesized in the manner described above.

For example, in the case of changing X, Y and Z to $H_2O$ and the like, the metal complex is reacted with water. Here, as a general indicator thereof, X, Y and Z are all $H_2O$ within a pH range of 1 to 3.5, one of X, Y and Z is $OH^-$ and the remaining two are $H_2O$ within a pH range of 3.5 to 7.8, and two or more of X, Y and Z are $OH^-$ at a pH of 7.8 or higher. Moreover, one or more of X, Y and Z is $O^{2-}$ at a pH of 12 or higher.

In the case of changing An1, for example, a reagent that provides a counter ion as previously explained (such as a nitrate ion, trifluoromethanesulfonate ion or sulfate ion) is reacted with the metal complex.

In the reactions for altering these X, Y, Z and An1, the reaction temperature is normally 5° C. to 200° C., the reaction pressure is normally 1 atm to 10 atm, and the reaction time is normally 1 hour to 48 hours.

[Hydrogen Peroxide Production Method]

As is explained below, the metal complex of the present invention as explained above can be used as a catalyst in a method for producing hydrogen peroxide by a novel mechanism.

In the method for producing hydrogen peroxide of the present invention, hydrogen peroxide is produced by going through a cycle consisting of sequentially converting the metal complex of the present invention to compounds represented by general formulas (2), (3) and (4) and then returning to the original compound represented by general formula (1) in a suitable reaction medium as explained below. The following provides an explanation of each conversion step.

<Step 1: Metal Complex Represented by General Formula (1)→Low Valence Metal Complex Represented by General Formula (2)>

In the method for producing hydrogen peroxide of the present invention, the metal complex of the present invention represented by general formula (1) is first reacted with hydrogen ($H_2$) as indicated by the following reaction formula to form a low valence metal complex represented by general formula (2).

[Chemical Formula 8]

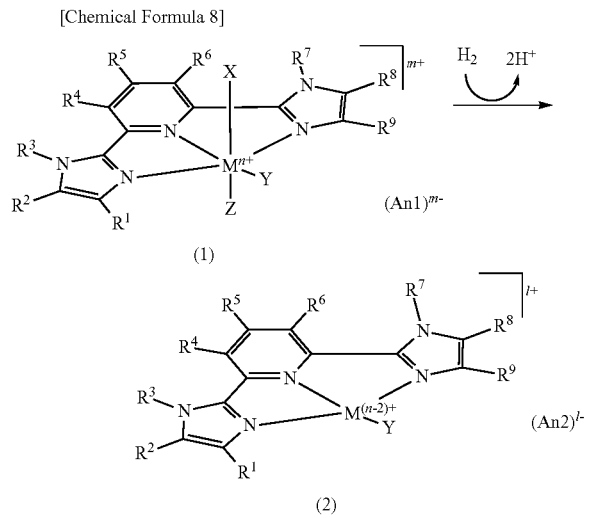

Furthermore, in general formula (2), M, n, $R^1$ to $R^9$ and Y are the same as defined in formula (1), 1+ represents the charge of the moiety of the metal complex excluding An2, An2 represents a counter ion that neutralizes the charge of the moiety, and the type, number and the like thereof are the same as An1. In addition, 1− represents the overall charge of An2. Furthermore, the low valence metal M can have a negative charge, and in that case, the charge 1+ of the moiety excluding An2 may also be negative. At that time, the counter ion An2 is a cation, and examples thereof include a sodium ion, lithium ion and tetraphenylphosphonium ion.

<Step 2: Low Valence Metal Complex Represented by Formula (2)→Binuclear Metal Complex Represented by General Formula (3)>

Next, the low valence metal complex represented by general formula (2) is oxidized by an oxidizing agent such as oxygen ($O_2$) resulting in the formation of a binuclear metal complex represented by general formula (3) as indicated in the following reaction formula.

[Chemical Formula 9]

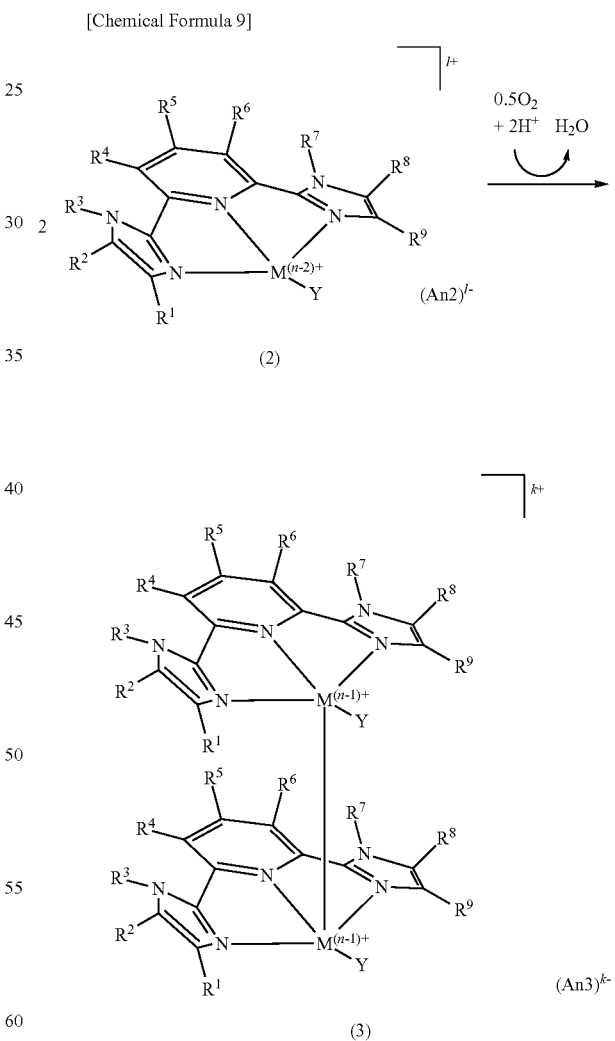

As a result of this reaction, a metal M accepts two electrons from a hydrogen molecule and thereby valence decreases by two resulting in a tetra-coordinated form. As a result, electrons derived from the hydrogen molecule are retained in the metal complex.

As a result, the valence of the metal M increases by one resulting in a penta-coordinated form. As a result of this reaction, half of the electrons retained in the metal (two of the four electrons retained in two low valence metal complexes) are incorporated in the oxidizing agent such as oxygen. The oxidizing agent that has incorporated the electrons couples with protons (H⁺) derived from the reaction medium or generated in Step 1. For example, water is released if the oxidizing agent is oxygen.

Furthermore, in general formula (3), M, n, $R^1$ to $R^9$ and Y are the same as defined in formula (1), k+ represents the charge of the moiety of the binuclear metal complex excluding An3, An3 represents a counter ion that neutralizes the charge of the moiety, and the type, number and the like thereof are the same as An1. In addition, k− represents the overall charge of An3. There are cases in which the charge k+ of the moiety of the binuclear metal complex excluding An3 is negative, and at that time, the counter ion An3 is a cation.

If a single compound is used for the metal complex represented by general formula (1) in Step 1, the upper metal complex moiety and the lower metal complex moiety in the binuclear metal complex represented by general formula (3) have the same structure. On the other hand, if a mixture of a plurality of compounds is used for the metal complex represented by general formula (1), the upper metal complex moiety and the lower metal complex moiety in the binuclear metal complex may be different.

In oxidizing the low valence metal complex represented by general formula (2), although known oxidizing agents such as oxygen, persulfuric acid, tert-butylhydroperoxide or iodosobenzene can be used without any special restrictions, from the viewpoint of subsequently carrying out the reaction by which the binuclear metal complex of general formula (3) is converted to a peroxo complex represented by general formula (4) in the following Step 3 or from the viewpoint of saving the bother of having to remove the oxidizing agent used in Step 2 from the reaction system, oxygen is preferably used as the oxidizing agent.

<Step 1 Binuclear Metal Complex Represented by General Formula (3)→Peroxo Complex Represented by General Formula (4)>

Next, following Step 2, the binuclear metal complex represented by general formula (3) is reacted with oxygen ($O_2$) and is converted to the peroxo complex represented by general formula (4) as indicated by the following reaction formula.

[Chemical Formula 10]

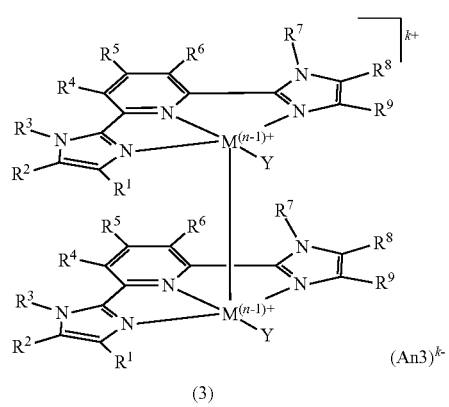

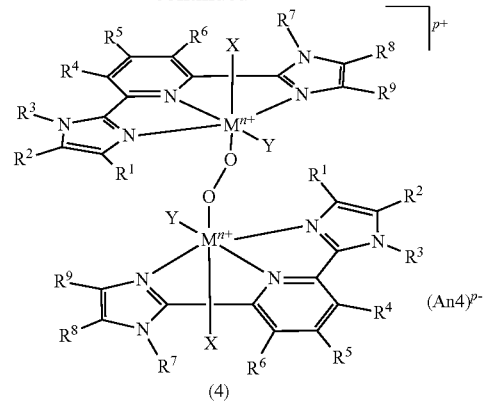

In this reaction, the two electrons present in the binuclear metal complex that were extracted from hydrogen in Step 1 are transferred from the metal M to oxygen and are retained in the —O—O— moiety. As a result, the valence of the metal M in the binuclear metal complex increases by 1 and it returns to the hexa-coordinated form.

Furthermore, in general formula (4), M, n, $R^1$ to $R^9$, X and Y are the same as defined in formula (1), p+ represents the charge of the moiety of the peroxo complex excluding An4, An4 represents a counter ion that neutralizes the charge of the moiety, and the type, number and the like thereof are the same as An1. In addition, p− represents the overall charge of An4.

Furthermore, in the case of using a mixture of a plurality of compounds for the metal complex represented by general formula (1) in Step 1, there are cases in which the structure of the upper metal complex moiety and the structure of the lower metal complex moiety in the peroxo complex may be different, as was previously described.

<Step 4: Peroxo Complex Represented by General Formula (4)→Metal Complex Represented by General Formula (1)>

Finally, the peroxo complex represented by general formula (4) is treated with a Lewis acid to let the complex react with protons (H⁺) derived from the acid, whereby releasing hydrogen peroxide ($H_2O_2$) as indicated by the following reaction formula.

[Chemical Formula 11]

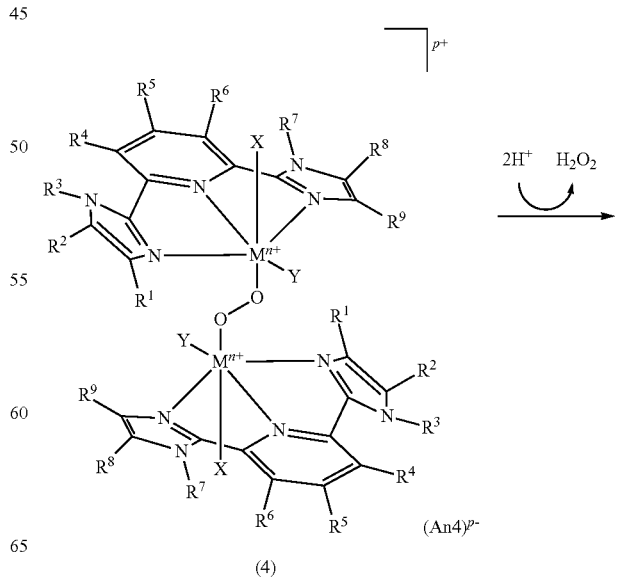

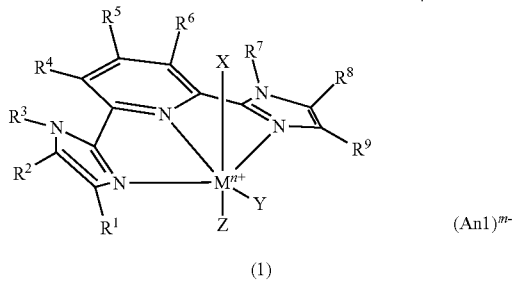

(1)

Examples of the Lewis acid include hydrochloric acid, sulfuric acid, nitric acid, trifluoromethanesulfonic acid, acetic acid, formic acid and tetrafluoroboric acid.

In addition, in Step 4, the proton donor in the form of the Lewis acid is not particularly required to be newly added, but rather protons derived from the reaction medium or residual protons generated in Step 1 (two of the four $H^+$ generated in association with formation of two molecules of low valence metal complex) can be used, and doing so is preferable from the viewpoints of cost and reaction simplicity.

The hydrogen peroxide formed is recovered after purifying by a conventionally known purification method such as extracting from a two-phase system consisting of organic solvent and water into an aqueous phase.

<Reaction Medium>

The method for producing hydrogen peroxide of the present invention is carried out in a suitable reaction medium. The reaction medium is normally a liquid phase and can be used without any particular limitations provided it does not inhibit the aforementioned reactions of the cycle of Steps 1 to 4 and dissolves the aforementioned metal complexes represented by general formulas (1) to (4). In the present invention, a reaction medium can be used by suitably selecting that which satisfies the aforementioned conditions from among conventionally used reaction media in the method for producing hydrogen peroxide by directly reacting hydrogen and oxygen.

Examples of the reaction medium include water; alcohols such as methanol and ethanol; aprotic polar solvents such as acetone, cyanomethane, DMF and DMSO; and mixed solvents thereof. Among these, water is preferable.

Moreover, these reaction media may contain an additive for adjusting pH, stabilizing effects or improving gas-solubility, and may also contain, for example, an acid such as phosphoric acid or sulfuric acid or a fluorine-based inert liquid.

<Example of Cycle of Hydrogen Peroxide Production Method>

The following provides an explanation of a specific embodiment of the method for producing hydrogen peroxide of the present invention based on a typical example of the cycle of the method for producing hydrogen peroxide of the present invention. The typical example of the cycle is as indicated below.

[Chemical Formula 12]

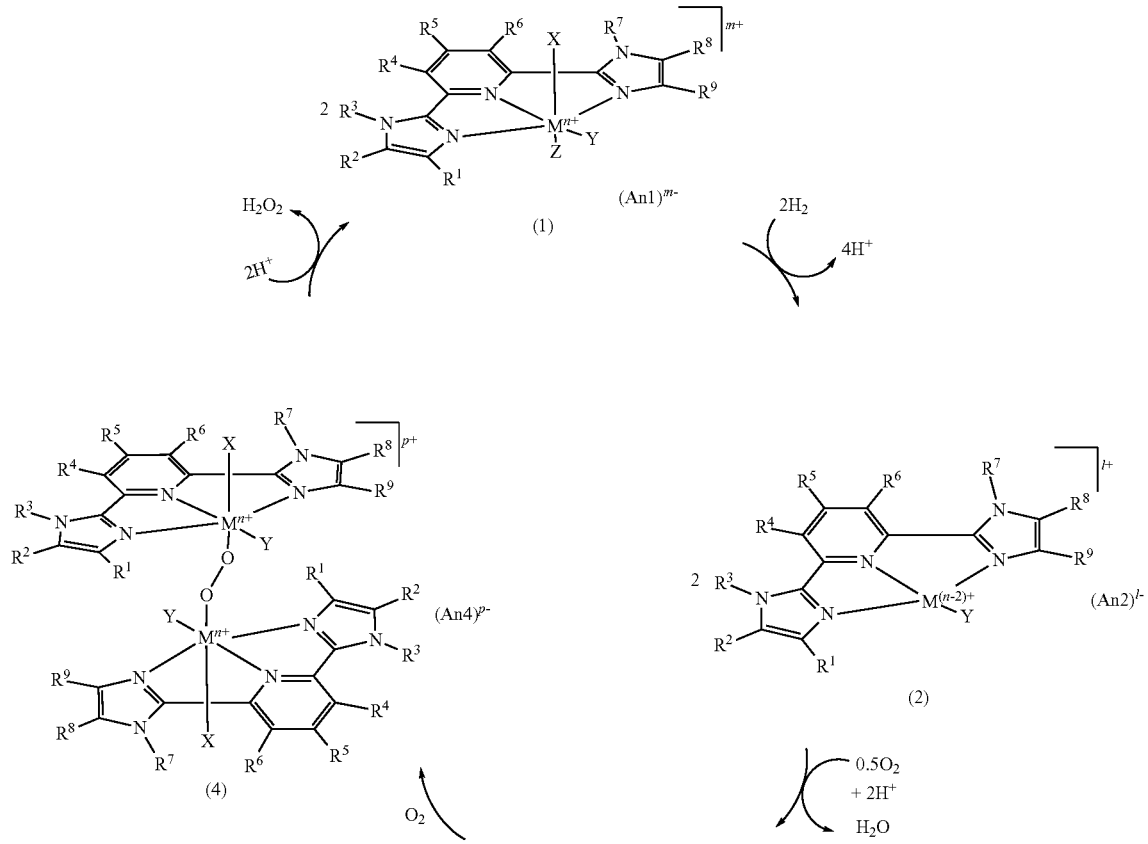

-continued

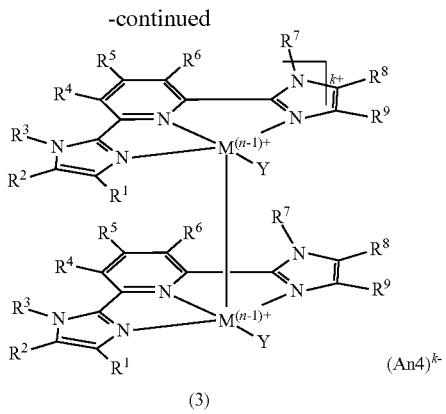

(3)

(Step 1)

In this cycle, the starting substance is the metal complex of the present invention represented by general formula (1), and this is dissolved in a suitable reaction medium. Since the metal complex functions as a homogeneous catalyst by dissolving in the reaction medium, the reaction can be carried out more efficiently than with conventional non-homogeneous catalysts.

Hydrogen gas is introduced into this reaction medium solution followed by carrying out Step 1 (wherein the metal complex and hydrogen molecules reacted in a 1:1 ratio) to cause electrons to be retained in the metal M, thereby obtaining the low valence metal complex of general formula (2). Here, unreacted hydrogen gas can be easily recovered by a suitable recovery means such as an aspiration means and reused.

(Step 2)

Next, Step 2 is carried out by introducing oxygen gas into the reaction medium solution of the low valence metal complex (oxidation reaction of low valence metal complex) to obtain the binuclear metal complex represented by general formula (3) whereby a portion of the electrons retained in the metal M in Step 1 are transferred to oxygen and water is released (0.5 molecules of oxygen react with two molecules of the low valence metal complex). If the reaction medium is water, since it does not occur that the reaction medium becomes heterogeneous as a result of this released water to have a detrimental effect on the formation efficiency of hydrogen peroxide, water is preferable as the reaction medium. The following explanation is based on the use of water as the reaction medium.

Although there is a risk of explosion if hydrogen (used in Step 1) and oxygen (used in Step 2) are present together, since that risk is eliminated if unreacted hydrogen gas is recovered in Step 1 as previously described, the method for producing hydrogen peroxide of the present invention is a method that is superior in terms of being extremely safe.

In addition, in the case of conventional methods for producing hydrogen peroxide, since hydrogen gas and oxygen gas are basically introduced simultaneously, these gases are used after being diluted with a diluting gas such as nitrogen in order to lower the risk of explosion. Since this type of dilution is not required in the present invention, it is advantageous in terms of cost, and since the amounts of hydrogen and oxygen used per unit reaction volume or per unit reaction time increase, there is a potential for improving hydrogen peroxide production efficiency.

(Step 3)

After having carried out Step 2, Step 3 is carried out by introducing oxygen gas into an aqueous solution of the binuclear metal complex represented by general formula (3) whereby residual electrons retained in the metal M migrate to oxygen (the binuclear metal complex and oxygen molecules react at a ratio of 1:1). As a result, the peroxo complex represented by general formula (4) is obtained.

Furthermore, this Step 3 can be carried out simultaneously with Step 2 if excess oxygen gas is introduced in Step 2. After having obtained the peroxo complex in this Step 3, unreacted oxygen gas can be recovered with a suitable recovery means such as an aspiration means and reused.

In addition, as a result of this recovery, the occurrence of an explosion can be avoided when Step 1 is again carried out to introduce hydrogen gas after continuing with the cycle through the next Step 4.

(Step 4)

As a result of reacting protons (H+) with the peroxo complex obtained in Step 3, hydrogen peroxide is obtained from the oxygen (—O—O—) that retained electrons in Step 3, and the metal complex represented by general formula (1) is regenerated. The protons may be supplied by separately adding a Lewis acid to the aqueous solution of the peroxo complex, protons derived from the reaction medium can be used, or residual protons generated in Step 1, a portion of which protons were used in Step 2, can be used. In this example, since water is the reaction medium, protons are supplied from the water or residual protons of Step 2 are used.

The hydrogen peroxide can be recovered with a known purification means as previously described, and hydrogen peroxide is produced continuously by proceeding with the cycle. Furthermore, although unreacted oxygen gas may be recovered in Step 3, it may also be recovered following completion of Step 4 immediately prior to Step 1 in which hydrogen gas is introduced.

As has been explained above, the method for producing hydrogen peroxide of the present invention produces hydrogen peroxide by the aforementioned reaction cycle consisting of Steps 1 to 4, and the reaction of each step can be carried out in a stepwise manner.

Namely, the reaction can be stopped at the point Step 1 is carried out or can be stopped at the point Step 2 is carried out, and the metal complex obtained in each reaction stage can be isolated. Since each step can be arbitrarily controlled in a stepwise manner in this way, it is easy to determine the current stage in the cycle, hydrogen gas or oxygen gas can be suitably introduced correspondingly, and recovery of these unreacted gases can be carried out precisely. Moreover, the reaction apparatuses can be separated for each step.

<Reaction Conditions>

Since the yield of hydrogen peroxide can be enhanced by setting the pressure to a high level (increasing the amounts of hydrogen and oxygen introduced) in the cycle of the method for producing hydrogen peroxide of the present invention explained above, the method is normally carried out using an autoclave or other pressure-resistant reaction apparatus.

The reaction apparatus of any type, for example, of an agitated vessel type, a bubble column type, a fixed bed type, or a microreactor type can be used as the reaction apparatus, and the reaction can be conducted either in a batchwise manner or in a continuous manner. The reaction apparatus has a gas introducing portion and a gas discharging portion (utilized for, e.g., recovery of unreacted hydrogen gas and unreacted oxygen gas), and further normally has, a thermometer and a pressure gauge, etc.

The reaction temperature during the cycle for synthesizing hydrogen peroxide in the present invention is preferably −80° C. to 100° C. and more preferably 10° C. to 30° C. Although there are no particular limitations on the reaction pressure, it is preferably 0.01 atm to 100 atm and more preferably 1 atm to 10 atm. In addition, the reaction time is normally 0.1 hour to 200 hours and preferably 1 hour to 50 hours.

In addition, although it is preferred that unreacted hydrogen gas is recovered following the introduction of hydrogen gas in Step 1 to prevent the occurrence of an explosion following subsequent introduction of oxygen gas in the present invention, as was previously described, hydrogen gas and oxygen gas may also be introduced simultaneously.

In this case, hydrogen peroxide is produced continuously by continuing to proceed through the aforementioned cycle without stopping at each stage. The flow rates of hydrogen gas and oxygen gas at this time are preferably such that the ratio thereof is that oxygen is in excess relative to hydrogen while avoiding the explosive range (such a ratio that the volumetric ratio of the flow rate of hydrogen gas to oxygen gas is within the range of 1:2 to 1:10). Moreover, from the viewpoint of safety, the hydrogen gas and oxygen gas are preferably diluted with an inert gas such as nitrogen gas in order to further lower the risk of explosion.

In addition, these gases are normally introduced into the liquid phase, or in other words, are introduced into the reaction medium solution from the viewpoint of reaction efficiency.

EXAMPLES

Although the following provides a more detailed explanation of the present invention through Examples, the present invention is not limited to them.

Example 1

Synthesis of $[Rh^{III}(iMP)Cl_3]$ $Rh^{III}Cl_3 \cdot 3H_2O$ (2.0 mmol) and iMP (2.1 mmol) (iMP=2,6-bis(1-methyl-1H-imidazol-2-yl)pyridine) were heated to reflux for 12 hours in ethanol to obtain $[Rh^{III}(iMP)Cl_3]$ (a compound of general formula (1) in which M is Rh, $R^1$, $R^2$, $R^4$, $R^5$, $R^6$, $R^8$ and $R^9$ are hydrogen atoms, $R^3$ and $R^7$ are methyl groups, and X, Y and Z are chloride ions) ($Rh^{III}Cl_3 \cdot 3H_2O$ is a commercially available product (rhodium trichloride trihydrate), and iMP was synthesized with reference to R. F. Carina, G. Bernardinelli and A. F. Williams, Angew. Chem. Int. Ed., 1993, 32, 1463).

Elementary analysis: theoretical values ($[Rh^{III}(iMP)Cl_3]$); C, 34.81%; H, 2.92%; N, 15.61%; measured values; C, 34.68%; H, 2.78%; N, 15.55%.

Example 2

Synthesis of $[Rh^{III}(iMP)(OH)(H_2O)_2](NO_3)_2$ {[1](NO_3)_2}

$AgNO_3$ (3.69 mmol) was added to the $[Rh^{III}(iMP)Cl_3]$ (1.23 mmol) obtained in Example 1 in water followed by refluxing for 12 hours at 100° C. to precipitate AgCl. When AgCl was removed by filtering the reaction solution followed by removing the water from the filtrate under reduced pressure, yellow powders were obtained. The yellow powders were then recrystallized using methanol to obtain yellow crystals.

Elementary analysis: theoretical values ($[1](NO_3)_2$); C, 35.10%; H, 3.14%; N, 13.65%; measured values; C, 34.92%; H, 3.12%; N, 13.61%.

Example 3

Synthesis of $[Rh^{I}(iMP)(H_2O)](NO_3)$ {[2](NO_3)} (Step 1)

The pH of an aqueous solution of $[1](NO_3)_2$ (0.92 mmol) obtained in Example 2 was adjusted to pH 6 using a 0.01 M aqueous nitric acid solution followed by introducing hydrogen (1 atm) into the aqueous solution at 25° C., allowing to react and gradually allowing a deep green solid to precipitate over the course of 24 hours. This precipitate was filtered and dried under reduced pressure to obtain a deep green solid.

Elementary analysis: theoretical values ($[2](NO_3)$); C, 43.29%; H, 3.15%; N, 13.46%; measured values; C, 43.40%; H, 3.25%; N, 13.63%.

Example 4

Synthesis of $[Rh^{II}_2(iMP)_2(H_2O)_4](NO_3)_4 \cdot H_2O$ {[3](NO_3)_4 \cdot H_2O} (Step 2)

Sodium nitrate (0.25 mmol) was added to the $[2](NO_3)$ (0.24 mmol) obtained in Example 3 followed by introducing oxygen (1 atm) into this suspended aqueous solution for 3 hours at 25° C. to obtain a red solution. The resulting solution was passed through Sephadex followed by removing the solvent under reduced pressure to obtain a red solid.

Elementary analysis: theoretical values ($[3](NO_3)_4 \cdot H_2O$); C, 34.57%; H, 3.09%; N, 13.44%; measured values; C, 34.66%; H, 2.92%; N, 13.46%.

Example 5

Synthesis of $[Rh^{III}_2(iMP)_2(H_2O)_4(\mu\text{-}\eta^1\text{:}\eta^1\text{-}O_2)](NO_3)_4$ {[4](NO_3)_4} (Step 3)

Oxygen (1 atm) was passed through an aqueous solution of the {[3](NO_3)_4 \cdot H_2O} (0.10 mmol) obtained in Example 4 for 3 hours at 25° C. after which the solution changed to a reddish-brown solution. The solvent was removed under reduced pressure to obtain a reddish-brown solid.

Elementary analysis: theoretical values ($[4](NO_3)_4$); C, 30.13%; H, 3.31%; N, 18.92%; measured values; C, 30.23%; H, 3.11%; N, 1.8.77%.

Example 6

Release of Hydrogen Peroxide (Step 4) and Detection

Nitric acid was added to an aqueous solution of the [4](NO$_3$)$_4$ (0.13 mmol) obtained in Example 5 at 25° C. followed by reacting for 3 hours and releasing hydrogen peroxide. Quantitative determination was carried out using a titanium complex and the yield of hydrogen peroxide was 3% based on the [4](NO$_3$)$_4$ obtained in Step 3 carried out immediately prior thereto (the method used to quantify hydrogen peroxide was the same method as that described in W. C. Wolfe, Anal. Chem. 1962, 34, 1328). Hydrogen peroxide yield was determined using the same standard in the following examples as well.

Example 7

Synthesis of [Cr$^{III}$(iMP)Cl$_3$]

Cr$^{III}$Cl$_3$ (2.0 mmol) and iMP (2.1 mmol) were mixed in ethanol to obtain [Cr$^{III}$(iMP)Cl$_3$] (Cr$^{III}$Cl$_3$ is a commercially available product (chromium trichloride)).

Elementary analysis: theoretical values ([Cr$^{III}$(iMP)Cl$_3$]); C, 39.27%; H, 3.30%; N, 17.61%; measured values; C, 39.53%; H, 3.51%; N, 17.39%.

Example 8

Synthesis of [Cr$^{III}$(iMP)(OH)(H$_2$O)$_2$](NO$_3$)$_2$ {[5](NO$_3$)$_2$}

AgNO$_3$ (3.0 mmol) was added to the [Cr$^{III}$(iMP)Cl$_3$] (1.0 mmol) obtained in Example 7 in water (temperature: 25° C.) followed by precipitation of AgCl. When AgCl was removed by filtering the reaction solution followed by removing the water from the filtrate under reduced pressure, yellow powders were obtained. The yellow powders were then recrystallized using methanol to obtain yellow crystals.

Elementary analysis: theoretical values ([5](NO$_3$)$_2$); C, 33.34%; H, 3.87%; N, 20.94%; measured values; C, 33.30%; H, 3.78%; N, 20.83%.

Example 9

Synthesis of [Cr$^{I}$(iMP)(H$_2$O)](NO$_3$) {[6](NO$_3$)} (Step 1)

The pH of an aqueous solution of the [5](NO$_3$)$_2$ (0.72 mmol) obtained in Example 8 was adjusted to pH 6 using a 0.01 M aqueous nitric acid solution followed by introducing hydrogen (1 atm) into the aqueous solution at 25° C. for 24 hours to obtain [6](NO$_3$).

Elementary analysis: theoretical values ([6](NO$_3$)); C, 42.05%; H, 4.07%; N, 22.63%; measured values; C, 42.18%; H, 3.99%; N, 22.47%.

Example 10

Synthesis of [Cr$^{II}_2$(iMP)$_2$(H$_2$O)$_4$](NO$_3$)$_4$ {[7](NO$_3$)$_4$} (Step 2)

Sodium nitrate (0.52 mmol) was added to a suspended aqueous solution of the [6](NO$_3$) (0.51 mmol) obtained in Example 9 followed by introducing oxygen (1 atm) for 3 hours at 25° C. to obtain a solution and passing the resulting solution through Sephadex and removing the solvent under reduced pressure to obtain [7](NO$_3$)$_4$.

Elementary analysis: theoretical values ([7](NO$_3$)$_4$); C, 34.60%; H, 3.80%; N, 21.72%; measured values; C, 34.67%; H, 3.89%; N, 21.66%.

Example 11

Synthesis of [Cr$^{III}_2$(iMP)$_2$(H$_2$O)$_4$($\mu$-$\eta^1$:$\eta^1$-O$_2$)](NO$_3$)$_4$ {[8](NO$_3$)$_4$} (Step 3)

Oxygen (1 atm) was passed through an aqueous solution of the [7](NO$_3$)$_4$ (0.25 mmol) obtained in Example 10 for 3 hours at 25° C. followed by removing the solvent under reduced pressure to obtain [8](NO$_3$)$_4$.

Elementary analysis: theoretical values ([8](NO$_3$)$_4$); C, 33.41%; H, 3.67%; N, 20.98%; measured values; C, 33.25%; H, 3.54%; N, 21.11%.

Example 12

Release of Hydrogen Peroxide (Step 4) and Detection

Nitric acid was added to an aqueous solution of the [8](NO$_3$)$_4$ (0.24 mmol) obtained in Example 11 at 25° C. followed by reacting for 3 hours and releasing hydrogen peroxide. Quantitative determination was carried out using a titanium complex and the yield of hydrogen peroxide was 1%.

Example 13

Synthesis of [Mn$^{III}$(iMP)Cl$_3$]

Mn$^{III}$Cl$_3$ (2.0 mmol) and iMP (2.1 mmol) were mixed in ethanol to obtain [Mn$^{III}$(iMP)Cl$_3$] (Mn$^{III}$Cl$_3$ is a commercially available product (manganese trichloride)).

Elementary analysis: theoretical values ([Mn$^{III}$(iMP)Cl$_3$]); C, 38.98%; H, 3.27%; N, 17.48%; measured values; C, 38.77%; H, 3.08%; N, 17.54%.

Example 14

Synthesis of [Mn$^{III}$(iMP)(OH)(H$_2$O)$_2$](NO$_3$)$_2$ {[9](NO$_3$)$_2$}

AgNO$_3$ (3.0 mmol) was added to the [Mn$^{III}$(iMP)Cl$_3$] (1.0 mmol) obtained in Example 13 in water (temperature: 25° C.) followed by precipitation of AgCl. AgCl was removed by filtering the reaction solution followed by removing the water from the filtrate under reduced pressure to obtain [9](NO$_3$)$_2$.

Elementary analysis: theoretical values ([9](NO$_3$)$_2$); C, 33.13%; H, 3.85%; N, 20.81%; measured values; C, 33.25%; H, 4.02%; N, 20.63%.

Example 15

Synthesis of [Mn$^{I}$(iMP)(H$_2$O)](NO$_3$) {[10](NO$_3$)} (Step 1)

The pH of an aqueous solution of the [9](NO$_3$)$_2$ (0.88 mmol) obtained in Example 14 was adjusted to pH 6 using a 0.01 M aqueous nitric acid solution followed by introducing hydrogen (1 atm) into the aqueous solution at 25° C. for 24 hours and allowing to react to obtain [10](NO$_3$).

Elementary analysis: theoretical values ([10](NO$_3$)); C, 41.72%; H, 4.04%; N, 22.46%; measured values; C, 41.80%; H, 4.18%; N, 22.55%.

Example 16

Synthesis of [Mn$^{II}_2$(iMP)$_2$(H$_2$O)$_4$](NO$_3$)$_4$ {[11](NO$_3$)$_4$} (Step 2)

Sodium nitrate (0.56 mmol) was added to a suspended aqueous solution of the [10](NO$_3$) (0.55 mmol) obtained in Example 15 followed by introducing oxygen (1 atm) for 3 hours at 25° C., passing the resulting solution through Sephadex and removing the solvent under reduced pressure to obtain [11](NO$_3$)$_4$.

Elementary analysis: theoretical values ([11](NO$_3$)$_4$); C, 34.37%; H, 3.77%; N, 21.58%; measured values; C, 34.58%; H, 3.91%; N, 21.48%.

Example 17

Synthesis of [Mn$^{III}_2$(iMP)$_2$(H$_2$O)$_4$(μ-η$^1$:η$^1$-O$_2$)](NO$_3$)$_4$ {[12](NO$_3$)$_4$} (Step 3)

Oxygen (1 atm) was passed through an aqueous solution of the {[11](NO$_3$)$_4$} (0.22 mmol) obtained in Example 16 for 3 hours at 25° C. after which the solution changed to a reddish-brown solution. The solvent was removed under reduced pressure to obtain a reddish-brown solid.

Elementary analysis: theoretical values ([12](NO$_3$)$_4$); C, 33.20%; H, 3.64%; N, 20.85%; measured values; C, 33.08%; H, 3.51%; N, 21.07%.

Example 18

Release of Hydrogen Peroxide (Step 4) and Detection

Nitric acid was added to an aqueous solution of the [12](NO$_3$)$_4$ (0.21 mmol) obtained in Example 17 at 25° C. followed by reacting for 3 hours and releasing hydrogen peroxide. Quantitative determination was carried out using a titanium complex and the yield of hydrogen peroxide was 1%.

Example 19

Synthesis of [Fe$^{III}$(iMP)Cl$_3$]

Fe$^{III}$Cl$_3$ (2.0 mmol) and iMP (2.1 mmol) were mixed in ethanol to obtain [Fe$^{III}$(iMP)Cl$_3$] (Fe$^{III}$Cl$_3$ is a commercially available product (iron trichloride)).

Elementary analysis: theoretical values ([Fe$^{III}$(iMP)Cl$_3$]); C, 38.89%; H, 3.26%; N, 17.44%; measured values; C, 38.77%; H, 3.09%; N, 17.21%.

Example 20

Synthesis of [Fe$^{III}$(iMP)(OH)(H$_2$O)$_2$](NO$_3$)$_2$ {[13](NO$_3$)$_2$}

AgNO$_3$ (3.0 mmol) was added to the [Fe$^{III}$(iMP)Cl$_3$] (1.0 mmol) obtained in Example 19 in water (temperature: 25° C.) followed by precipitation of AgCl. AgCl was removed by filtering the reaction solution followed by removing the water from the filtrate under reduced pressure to obtain [13](NO$_3$)$_2$.

Elementary analysis: theoretical values ([13](NO$_3$)$_2$); C, 33.07%; H, 3.84%; N, 20.77%; measured values; C, 32.98%; H, 4.01%; N, 20.60%.

Example 21

Synthesis of [Fe$^{I}$(iMP)(H$_2$O)](NO$_3$)([14](NO$_3$)) (Step 1)

The pH of an aqueous solution of the [13](NO$_3$)$_2$ (0.90 mmol) obtained in Example 20 was adjusted to pH 6 using a 0.01 M aqueous nitric acid solution followed by introducing hydrogen (1 atm) into the aqueous solution at 25° C. for 24 hours and allowing to react to obtain [14](NO$_3$).

Elementary analysis: theoretical values ([14](NO$_3$)); C, 41.62%; H, 4.03%; N, 22.40%; measured values; C, 41.54%; H, 3.97%; N, 22.27%.

Example 22

Synthesis of [Fe$^{II}_2$(iMP)$_2$(H$_2$O)$_4$](NO$_3$)$_4$ {[15](NO$_3$)$_4$} (Step 2)

Sodium nitrate (0.72 mmol) was added to a suspended aqueous solution of the [14](NO$_3$) (0.71 mmol) obtained in Example 21 followed by introducing oxygen (1 atm) for 3 hours at 25° C., passing the resulting solution through Sephadex and removing the solvent under reduced pressure to obtain [15](NO$_3$)$_4$.

Elementary analysis: theoretical values ([15](NO$_3$)$_4$); C, 34.30%; H, 3.76%; N, 21.54%; measured values; C, 34.17%; H, 3.58%; N, 21.56%.

Example 23

Synthesis of [Fe$^{III}_2$(iMP)$_2$(H$_2$O)$_4$(μ-η$^1$:η$^1$-O$_2$)](NO$_3$)$_4$ {[16](NO$_3$)$_4$} (Step 3)

Oxygen (1 atm) was passed through an aqueous solution of the {[15](NO$_3$)$_4$} (0.35 mmol) obtained in Example 22 for 3 hours at 25° C. followed by removing the solvent under reduced pressure to obtain [16](NO$_3$)$_4$.

Elementary analysis: theoretical values ([16](NO$_3$)$_4$); C, 33.14%; H, 3.64%; N, 20.81%; measured values; C, 33.31%; H, 3.78%; N, 20.66%.

Example 24

Release of Hydrogen Peroxide (Step 4) and Detection

Nitric acid was added to an aqueous solution of the [16](NO$_3$)$_4$ (0.34 mmol) obtained in Example 23 at 25° C. followed by reacting for 3 hours and releasing hydrogen peroxide. Quantitative determination was carried out using a titanium complex and the yield of hydrogen peroxide was 1%.

Example 25

Synthesis of [Co$^{III}$(iMP)Cl$_3$]

Co$^{III}$Cl$_3$ (2.0 mmol) and iMP (2.1 mmol) were mixed in ethanol to obtain [Co$^{III}$(iMP)Cl$_3$] (Co$^{III}$Cl$_3$ is a commercially available product (cobalt trichloride)).

Elementary analysis: theoretical values ([$Co^{III}$(iMP)$Cl_3$]); C, 38.59%; H, 3.24%; N, 17.31%; measured values; C, 38.45%; H, 3.01%; N, 17.15%.

Example 26

Synthesis of [$Co^{III}$(iMP)(OH)($H_2O$)$_2$]($NO_3$)$_2$ {[17]($NO_3$)$_2$}

$AgNO_3$ (3.0 mmol) was added to the [$Co^{III}$(iMP)$Cl_3$] (1.0 mmol) obtained in Example 25 in water (temperature: 25° C.) followed by precipitation of AgCl. AgCl was removed by filtering the reaction solution followed by removing the water from the filtrate under reduced pressure to obtain [17]($NO_3$)$_2$.

Elementary analysis: theoretical values ([17]($NO_3$)$_2$); C, 32.85%; H, 3.82%; N, 20.63%; measured values; C, 32.99%; H, 3.70%; N, 20.52%.

Example 27

Synthesis of [$Co^I$(iMP)($H_2O$)]($NO_3$) {[18]($NO_3$)} (Step 1)

The pH of an aqueous solution of the [17]($NO_3$)$_2$ (0.91 mmol) obtained in Example 26 was adjusted to pH 6 using a 0.01 M aqueous nitric acid solution followed by introducing hydrogen (1 atm) into the aqueous solution at 25° C. for 24 hours and allowing to react to obtain [18]($NO_3$).

Elementary analysis: theoretical values ([18]($NO_3$)); C, 41.28%; H, 4.00%; N, 22.22%; measured values; C, 41.35%; H, 4.23%; N, 22.03%.

Example 28

Synthesis of [$Co^{II}_2$(iMP)$_2$($H_2O$)$_4$]($NO_3$)$_4$ {[19]($NO_3$)$_4$} (Step 2)

Sodium nitrate (0.74 mmol) was added to a suspended aqueous solution of the [18]($NO_3$) (0.75 mmol) obtained in Example 27 followed by introducing oxygen (1 atm) for 3 hours at 25° C., passing the resulting solution through Sephadex and removing the solvent under reduced pressure to obtain [19]($NO_3$)$_4$.

Elementary analysis: theoretical values ([19]($NO_3$)$_4$); C, 34.07%; H, 3.74%; N, 21.40%; measured values; C, 34.21%; H, 3.80%; N, 21.29%.

Example 29

Synthesis of [$Co^{III}_2$(iMP)$_2$($H_2O$)$_4$($\alpha$-$\eta^1$:$\eta^1$-$O_2$)]($NO_3$)$_4$ {[20]($NO_3$)$_4$} (Step 3)

Oxygen (1 atm) was passed through an aqueous solution of the [19]($NO_3$)$_4$ (0.27 mmol) obtained in Example 28 for 3 hours at 25° C. followed by removing the solvent under reduced pressure to obtain [20]($NO_3$)$_4$.

Elementary analysis: theoretical values ([20]($NO_3$)$_4$); C, 32.92%; H, 3.61%; N, 20.67%; measured values; C, 32.88%; H, 3.52%; N, 20.83%.

Example 30

Release of Hydrogen Peroxide (Step 4) and Detection

Nitric acid was added to an aqueous solution of the [20]($NO_3$)$_4$ (0.26 mmol) obtained in Example 29 at 25° C. followed by reacting for 3 hours and releasing hydrogen peroxide. Quantitative determination was carried out using a titanium complex and the yield of hydrogen peroxide was 1%.

Example 31

Synthesis of [$Ni^{II}$(iMP)$Cl_2$]

$Ni^{II}Cl_2$ (2.0 mmol) and iMP (2.1 mmol) were mixed in ethanol to obtain [$Ni^{II}$(iMP)$Cl_2$] ($Ni^{II}Cl_2$ is a commercially available product (nickel dichloride)).

Elementary analysis: theoretical values ([$Ni^{II}$(iMP)$Cl_2$]): C, 42.33%; H, 3.55%; N, 18.99%; measured values: C, 42.39%; H, 3.37%; N, 19.18%.

Example 32

Synthesis of [$Ni^{II}$(iMP)(OH)($H_2O$)$_2$]($NO_3$) {[21]($NO_3$)}

$AgNO_3$ (2.0 mmol) was added to the [$Ni^{II}$(iMP)$Cl_2$] (1.0 mmol) obtained in Example 31 in water (temperature: 25° C.) followed by precipitation of AgCl. AgCl was removed by filtering the reaction solution followed by removing the water from the filtrate under reduced pressure to obtain [21]($NO_3$).

Elementary analysis: theoretical values ([21]($NO_3$)); C, 37.80%; H, 4.39%; N, 20.35%; measured values; C, 37.70%; H, 4.21%; N, 20.24%.

Example 33

Synthesis of [$Ni^0$(iMP)($H_2O$)] {[22]} (Step 1)

The pH of an aqueous solution of the [21]($NO_3$)(0.90 mmol) obtained in Example 32 was adjusted to pH 6 using a 0.01 M aqueous nitric acid solution followed by introducing hydrogen (1 atm) into the aqueous solution at 25° C. for 24 hours and allowing to react to obtain [22].

Elementary analysis: theoretical values ([22]); C, 49.41%; H, 4.78%; N, 22.16%; measured values; C, 41.25%; H, 4.16%; N, 15.34%.

Example 34

Synthesis of [$Ni^I_2$(iMP)$_2$($H_2O$)$_4$]($NO_3$)$_2$ {[23]($NO_3$)$_2$} (Step 2)

Sodium nitrate (0.78 mmol) was added to a suspended aqueous solution of the [22] (0.77 mmol) obtained in Example 33 followed by introducing oxygen (1 atm) for 3 hours at 25° C., passing the resulting solution through Sephadex and removing the solvent under reduced pressure to obtain [23]($NO_3$)$_2$.

Elementary analysis: theoretical values ([23]($NO_3$)$_2$); C, 40.81%; H, 5.14%; N, 20.40%; measured values; C, 40.65%; H, 4.94%; N, 20.68%.

Example 35

Synthesis of [$Ni^{II}_2$(iMP)$_2$($H_2O$)$_4$($\mu$-$\eta^1$:$\eta^1$-$O_2$)]($NO_3$)$_2$ {[24]($NO_3$)$_2$} (Step 3)

Oxygen (1 atm) was passed through an aqueous solution of the {[23]($NO_3$)$_2$} (0.38 mmol) obtained in Example 34 for 3 hours at 25° C. followed by removing the solvent from the resulting solution under reduced pressure to obtain [24](NO$_3$)$_2$.

Elementary analysis: theoretical values ([24](NO$_3$)$_2$); C, 37.90%; H, 4.16%; N, 20.40%; measured values; C, 37.79%; H, 4.22%; N, 20.60%.

Example 36

Release of Hydrogen Peroxide (Step 4) and Detection

Nitric acid was added to an aqueous solution of the [24](NO$_3$)$_2$ (0.37 mmol) obtained in Example 35 at 25° C. followed by reacting for 3 hours and releasing hydrogen peroxide. Quantitative determination was carried out using a titanium complex and the yield of hydrogen peroxide was 1%.

Example 37

Synthesis of [Cu$^{II}$(iMP)Cl$_2$]

Cu$^{II}$Cl$_2$ (2.0 mmol) and iMP (2.1 mmol) were mixed in ethanol to obtain [Cu$^{II}$(iMP)Cl$_2$] (Cu$^{II}$Cl$_2$ is a commercially available product (copper chloride)).

Elementary analysis: theoretical values ([Cu$^{II}$(iMP)Cl$_2$]): C, 41.78%; H, 3.51%; N, 18.74%; measured values: C, 41.61%; H, 3.35%; N, 18.98%.

Example 38

Synthesis of [Cu$^{II}$(iMP)(OH)(H$_2$O)$_2$](NO$_3$) {[25](NO$_3$)}

AgNO$_3$ (2.0 mmol) was added to the [Cu$^{II}$(iMP)Cl$_2$] (1.0 mmol) obtained in Example 37 in water (temperature: 25° C.) followed by precipitation of AgCl. AgCl was removed by filtering the reaction solution followed by removing the water from the filtrate under reduced pressure to obtain [25](NO$_3$).

Elementary analysis: theoretical values ([25](NO$_3$)); C, 37.37%; H, 4.34%; N, 20.11%; measured values; C, 37.50%; H, 4.39%; N, 20.00%.

Example 39

Synthesis of [Cu$^0$(iMP)(H$_2$O)] {[26]} (Step 1)

The pH of an aqueous solution of the [25](NO$_3$) (0.88 mmol) obtained in Example 38 was adjusted to pH 6 using a 0.01 M aqueous nitric acid solution followed by introducing hydrogen (1 atm) into the aqueous solution at 25° C. for 24 hours and allowing to react to obtain [26].

Elementary analysis: theoretical values ([26]); C, 48.67%; H, 4.71%; N, 21.83%; measured values; C, 48.90%; H, 4.60%; N, 22.07%.

Example 40

Synthesis of [Cu$^I_2$(iMP)$_2$(H$_2$O)$_4$](NO$_3$)$_2$ {[27](NO$_3$)$_2$} (Step 2)

Sodium nitrate (0.67 mmol) was added to a suspended aqueous solution of the [26] (0.66 mmol) obtained in Example 39 followed by introducing oxygen (1 atm) for 3 hours at 25° C., passing the resulting solution through Sephadex and removing the solvent under reduced pressure to obtain [27](NO$_3$)$_2$.

Elementary analysis: theoretical values ([27](NO$_3$)$_2$); C, 38.95%; H, 4.27%; N, 20.97%; measured values; C, 38.71%; H, 4.55%; N, 21.06%.

Example 41

Synthesis of [Cu$^{II}_2$(iMP)$_2$(H$_2$O)$_4$(μ-η$^1$:η$^1$-O$_2$)](NO$_3$)$_2$ {[28](NO$_3$)$_2$} (Step 3)

Oxygen (1 atm) was passed through an aqueous solution of the [27](NO$_3$)$_2$ (0.33 mmol) obtained in Example 40 for 3 hours at 25° C. followed by removing the solvent under reduced pressure to obtain [28](NO$_3$)$_2$.

Elementary analysis: theoretical values ([28](NO$_3$)$_2$); C, 37.46%; H, 4.11%; N, 20.16%; measured values; C, 37.30%; H, 4.24%; N, 20.01%.

Example 42

Release of Hydrogen Peroxide (Step 4) and Detection

Nitric acid was added to an aqueous solution of the [28](NO$_3$)$_2$ (0.32 mmol) obtained in Example 41 at 25° C. followed by reacting for 3 hours and releasing hydrogen peroxide. Quantitative determination was carried out using a titanium complex and the yield of hydrogen peroxide was 1%.

Example 43

Synthesis of [Mo$^{III}$(iMP)Cl$_3$]

Mo$^{III}$Cl$_3$ (2.0 mmol) and iMP (2.1 mmol) were mixed in ethanol to obtain [Mo$^{III}$(iMP)Cl$_3$] (Mo$^{III}$Cl$_3$ is a commercially available product (molybdenum trichloride)).

Elementary analysis: theoretical values ([Mo$^{III}$(iMP)Cl$_3$]); C, 35.36%; H, 2.97%; N, 15.86%; measured values; C, 35.11%; H, 2.79%; N, 15.65%.

Example 44

Synthesis of [Mo$^{III}$(iMP)(OH)(H$_2$O)$_2$](NO$_3$)$_2$ {[29](NO$_3$)$_2$}

AgNO$_3$ (3.0 mmol) was added to the [Mo$^{III}$(iMP)Cl$_3$] (1.0 mmol) obtained in Example 43 in water (temperature: 25° C.) followed by precipitation of AgCl. AgCl was removed by filtering the reaction solution followed by removing the water from the filtrate under reduced pressure to obtain [29](NO$_3$)$_2$.

Elementary analysis: theoretical values ([29](NO$_3$)$_2$); C, 30.48%; H, 3.54%; N, 19.14%; measured values; C, 30.60%; H, 3.47%; N, 19.07%.

Example 45

Synthesis of [Mo$^I$(iMP)(H$_2$O)](NO$_3$) {[30](NO$_3$)} (Step 1)

The pH of an aqueous solution of the [29](NO$_3$)$_2$ (0.91 mmol) obtained in Example 44 was adjusted to pH 6 using a 0.01 M aqueous nitric acid solution followed by introducing hydrogen (1 atm) into the aqueous solution at 25° C. for 24 hours and allowing to react to obtain [30]($NO_3$).

Elementary analysis: theoretical values ([30]($NO_3$)); C, 37.60%; H, 3.64%; N, 20.24%; measured values; C, 37.50%; H, 3.81%; N, 20.03%.

Example 46

Synthesis of [$Mo^{II}_2$(iMP)$_2$($H_2O$)$_4$]($NO_3$)$_4$ {[31]($NO_3$)$_4$} (Step 2)

Sodium nitrate (0.72 mmol) was added to a suspended aqueous solution of the [30]($NO_3$) (0.71 mmol) obtained in Example 45 followed by introducing oxygen (1 atm) for 3 hours at 25° C., passing the resulting solution through Sephadex and removing the solvent under reduced pressure to obtain [31]($NO_3$)$_4$.

Elementary analysis: theoretical values ([31]($NO_3$)$_4$); C, 31.53%; H, 3.46%; N, 19.80%; measured values; C, 31.39%; H, 3.25%; N, 19.62%.

Example 47

Synthesis of [$Mo^{III}_2$(iMP)$_2$($H_2O$)$_4$($\mu$-$\eta^1$:$\eta^1$-$O_2$)]($NO_3$)$_4$ {[32]($NO_3$)$_4$} (Step 3)

Oxygen (1 atm) was passed through an aqueous solution of the [31]($NO_3$)$_4$ (0.35 mmol) obtained in Example 46 for 3 hours at 25° C. followed by removing the solvent under reduced pressure to obtain [32]($NO_3$)$_4$.

Elementary analysis: theoretical values ([32]($NO_3$)$_4$); C, 30.54%; H, 3.35%; N, 19.18%; measured values; C, 30.41%; H, 3.21%; N, 19.32%.

Example 48

Release of Hydrogen Peroxide (Step 4) and Detection

Nitric acid was added to an aqueous solution of the [32]($NO_3$)$_4$ (0.34 mmol) obtained in Example 47 at 25° C. followed by reacting for 3 hours and releasing hydrogen peroxide. Quantitative determination was carried out using a titanium complex and the yield of hydrogen peroxide was 1%.

Example 49

Synthesis of [$Ru^{III}$(iMP)$Cl_3$]

$Ru^{III}Cl_3$ (2.0 mmol) and iMP (2.1 mmol) were heated to reflux in ethanol to obtain [$Ru^{III}$(iMP)$Cl_3$] ($Ru^{III}Cl_3$ is a commercially available product (ruthenium trichloride)).

Elementary analysis: theoretical values ([$Ru^{III}$(iMP)$Cl_3$]); C, 34.95%; H, 2.93%; N, 15.68%; measured values; C, 34.88%; H, 2.76%; N, 15.53%.

Example 50

Synthesis of [$Ru^{III}$(iMP)(OH)($H_2O$)$_2$]($NO_3$)$_2$ {[33]($NO_3$)$_2$}

$AgNO_3$ (3.0 mmol) was added to the [$Ru^{III}$(iMP)$Cl_3$] (1.0 mmol) obtained in Example 49 in water followed by refluxing for 12 hours at 100° C. and precipitation of AgCl. AgCl was removed by filtering the reaction solution followed by removing the water from the filtrate under reduced pressure to obtain [33]($NO_3$)$_2$.

Elementary analysis: theoretical values ([33]($NO_3$)$_2$); C, 30.18%; H, 3.51%; N, 18.95%; measured values; C, 30.30%; H, 3.41%; N, 18.83%.

Example 51

Synthesis of [$Ru^I$(iMP)($H_2O$)]($NO_3$) {[34]($NO_3$)} (Step 1)

The pH of an aqueous solution of the [33]($NO_3$)$_2$ (0.85 mmol) obtained in Example 50 was adjusted to pH 6 using a 0.01 M aqueous nitric acid solution followed by introducing hydrogen (1 atm) into the aqueous solution at 25° C. for 24 hours and allowing to react to obtain [34]($NO_3$).

Elementary analysis: theoretical values ([34]($NO_3$)); C, 37.14%; H, 3.60%; N, 19.99%; measured values; C, 37.01%; H, 3.77%; N, 19.86%.

Example 52

Synthesis of [$Ru^{II}_2$(iMP)$_2$($H_2O$)$_4$]($NO_3$)$_4$ {[35]($NO_3$)$_4$} (Step 2)

Sodium nitrate (0.64 mmol) was added to a suspended aqueous solution of the [34]($NO_3$) (0.63 mmol) obtained in Example 51 followed by introducing oxygen (1 atm) for 3 hours at 25° C., passing the resulting solution through Sephadex and removing the solvent under reduced pressure to obtain [35]($NO_3$)$_4$.

Elementary analysis: theoretical values ([35]($NO_3$)$_4$); C, 31.20%; H, 3.42%; N, 19.59%; measured values; C, 31.04%; H, 3.21%; N, 19.43%.

Example 53

Synthesis of [$Ru^{III}_2$(iMP)$_2$($H_2O$)$_4$($\mu$-$\eta^1$:$\eta^1$-$O_2$)]($NO_3$)$_4$ {[36]($NO_3$)$_4$} (Step 3)

Oxygen (1 atm) was passed through an aqueous solution of the [35]($NO_3$)$_4$ (0.31 mmol) obtained in Example 52 for 3 hours at 25° C. followed by removing the solvent under reduced pressure to obtain [36]($NO_3$)$_4$.

Elementary analysis: theoretical values ([36]($NO_3$)$_4$); C, 30.24%; H, 3.32%; N, 18.99%; measured values; C, 30.09%; H, 3.18%; N, 19.05%.

Example 54

Release of Hydrogen Peroxide (Step 4) and Detection

Nitric acid was added to an aqueous solution of the [36]($NO_3$)$_4$ (0.30 mmol) obtained in Example 53 at 25° C. followed by reacting for 3 hours and releasing hydrogen peroxide. Quantitative determination was carried out using a titanium complex and the yield of hydrogen peroxide was 1%.

Example 55

Synthesis of [$Pd^{II}$(iMP)$Cl_2$]

$Pd^{II}Cl_2$ (2.0 mmol) and iMP (2.1 mmol) were heated to reflux in ethanol to obtain [$Pd^{II}$(iMP)$Cl_2$] ($Pd^{II}Cl_2$ is a commercially available product (palladium dichloride)).

Elementary analysis: theoretical values ([Pd$^{II}$(iMP)Cl$_2$]); C, 37.48%; H, 3.15%; N, 16.81%; measured values; C, 37.32%; H, 2.96%; N, 16.63%.

Example 56

Synthesis of [Pd$^{II}$(iMP)(OH)(H$_2$O)$_2$](NO$_3$) {[37](NO$_3$)}

AgNO$_3$ (2.0 mmol) was added to the [Pd$^{II}$(iMP)Cl$_2$] (1.0 mmol) obtained in Example 55 in water followed by refluxing for 12 hours at 100° C. and precipitation of AgCl. AgCl was removed by filtering the reaction solution followed by removing the water from the filtrate under reduced pressure to obtain [37](NO$_3$).

Elementary analysis: theoretical values ([37](NO$_3$)); C, 33.89%; H, 3.94%; N, 18.24%; measured values; C, 33.79%; H, 3.87%; N, 18.33%.

Example 57

Synthesis of [Pd$^0$(iMP)(H$_2$O)] {[38]} (Step 1)

The pH of an aqueous solution of the [37](NO$_3$) (0.88 mmol) obtained in Example 56 was adjusted to pH 6 using a 0.01 M aqueous nitric acid solution followed by introducing hydrogen (1 atm) into the aqueous solution at 25° C. for 24 hours and allowing to react to obtain [38].

Elementary analysis: theoretical values ([38]); C, 42.93%; H, 4.16%; N, 19.26%; measured values; C, 42.90%; H, 3.95%; N, 19.46%.

Example 58

Synthesis of [Pd$^I_2$(iMP)$_2$(H$_2$O)$_4$](NO$_3$)$_2$ {[39](NO$_3$)$_2$} (Step 2)

Sodium nitrate (0.72 mmol) was added to a suspended aqueous solution of the [38] (0.71 mmol) obtained in Example 57 followed by introducing oxygen (1 atm) for 3 hours at 25° C., passing the resulting solution through Sephadex and removing the solvent under reduced pressure to obtain [39](NO$_3$)$_2$.

Elementary analysis: theoretical values ([39](NO$_3$)$_2$); C, 35.19%; H, 3.86%; N, 18.94%; measured values; C, 34.99%; H, 3.75%; N, 19.16%.

Example 59

Synthesis of [Pd$^{II}_2$(iMP)$_2$(H$_2$O)$_4$(µ-η$^1$:η$^1$-O$_2$)](NO$_3$)$_2$ {[40](NO$_3$)$_2$} (Step 3)

Oxygen (1 atm) was passed through an aqueous solution of the [39](NO$_3$)$_2$ (0.35 mmol) obtained in Example 58 for 3 hours at 25° C. followed by removing the solvent under reduced pressure to obtain [40](NO$_3$)$_2$.

Elementary analysis: theoretical values ([40](NO$_3$)$_2$); C, 33.96%; H, 3.73%; N, 18.28%; measured values; C, 33.82%; H, 3.53%; N, 18.01%.

Example 60

Release of Hydrogen Peroxide (Step 4) and Detection

Nitric acid was added to an aqueous solution of the [40](NO$_3$)$_2$ (0.34 mmol) obtained in Example 59 at 25° C. followed by reacting for 3 hours and releasing hydrogen peroxide. Quantitative determination was carried out using a titanium complex and the yield of hydrogen peroxide was 1%.

Example 61

Synthesis of [Ag$^I$(iMP)Cl]

Ag$^I$Cl (2.0 mmol) and iMP (2.1 mmol) were heated to reflux in ethanol to obtain [Ag$^I$(iMP)Cl] (Ag$^I$Cl is a commercially available product (silver chloride)).

Elementary analysis: theoretical values ([Ag$^I$(iMP)Cl]); C, 42.18%; H, 4.30%; N, 17.57%; measured values; C, 42.29%; H, 4.51%; N, 17.33%.

Example 62

Synthesis of [Ag$^I$(iMP)(OH)(H$_2$O)$_2$] {[41]}

AgNO$_3$ (1.0 mmol) was added to the [Ag$^I$(iMP)Cl] (1.0 mmol) obtained in Example 61 in water followed by refluxing for 12 hours at 100° C. and precipitation of AgCl. AgCl was removed by filtering the reaction solution followed by removing the water from the filtrate under reduced pressure to obtain [41].

Elementary analysis: theoretical values ([41]); C, 39.02%; H, 4.53%; N, 17.50%; measured values; C, 39.16%; H, 4.73%; N, 18.05%.

Example 63

Synthesis of [Ag$^0$(iMP)(H$_2$O)] {[42]} (Step 1)

The pH of an aqueous solution of the [41] (0.86 mmol) obtained in Example 62 was adjusted to pH 6 using a 0.01 M aqueous nitric acid solution followed by introducing hydrogen (1 atm) into the aqueous solution at 25° C. for 24 hours and allowing to react to obtain [42].

Elementary analysis: theoretical values ([42]); C, 42.76%; H, 4.14%; N, 19.18%; measured values; C, 42.52%; H, 3.91%; N, 19.04%.

Example 64

Synthesis of [Ag$^I_2$(iMP)$_2$(H$_2$O)$_4$](NO$_3$)$_2$ {[43](NO$_3$)$_2$} (Step 2)

Sodium nitrate (0.56 mmol) was added to a suspended aqueous solution of the [42] (0.55 mmol) obtained in Example 63 followed by introducing oxygen (1 atm) for 3 hours at 25° C., passing the resulting solution through Sephadex and removing the solvent under reduced pressure to obtain [43](NO$_3$)$_2$.

Elementary analysis: theoretical values ([43](NO$_3$)$_2$); C, 35.07%; H, 3.85%; N, 18.88%; measured values; C, 35.26%; H, 3.66%; N, 19.01%.

Example 65

Synthesis of [Ag$^{II}_2$(iMP)$_2$(H$_2$O)$_4$(µ-η$^1$:η$^1$-O$_2$)](NO$_3$)$_2$ {[44](NO$_3$)$_2$} (Step 3)

Oxygen (1 atm) was passed through an aqueous solution of the [43](NO$_3$)$_2$ (0.27 mmol) obtained in Example 64 for 3 hours at 25° C. followed by removing the solvent under reduced pressure to obtain [44](NO$_3$)$_2$.

Elementary analysis: theoretical values ([44](NO$_3$)$_2$); C, 33.86%; H, 3.72%; N, 18.22%; measured values; C, 33.77%; H, 3.59%; N, 18.34%.

Example 66

Release of Hydrogen Peroxide (Step 4) and Detection

Nitric acid was added to an aqueous solution of the [44](NO$_3$)$_2$ (0.26 mmol) obtained in Example 65 at 25° C. followed by reacting for 3 hours and releasing hydrogen peroxide. Quantitative determination was carried out using a titanium complex and the yield of hydrogen peroxide was 1%.

Example 67

Synthesis of [W$^{III}$(iMP)Cl$_3$]

W$^{III}$Cl$_3$ (2.0 mmol) and iMP (2.1 mmol) were heated to reflux in ethanol to obtain [W$^{III}$(iMP)Cl$_3$] (W$^{III}$Cl$_3$ is a commercially available product (tungsten trichloride)).
Elementary analysis: theoretical values ([W$^{III}$(iMP)Cl$_3$]); C, 29.49%; H, 2.47%; N, 13.23%; measured values; C, 29.61%; H, 2.44%; N, 13.13%.

Example 68

Synthesis of [W$^{III}$(iMP)(OH)(H$_2$O)$_2$](NO$_3$)$_2$ {[45](NO$_3$)$_2$}

AgNO$_3$ (3.0 mmol) was added to the [W$^{III}$(iMP)Cl$_3$] (1.0 mmol) obtained in Example 67 in water followed by refluxing for 12 hours at 100° C. and precipitation of AgCl. AgCl was removed by filtering the reaction solution followed by removing the water from the filtrate under reduced pressure to obtain [45](NO$_3$)$_2$.
Elementary analysis: theoretical values ([45](NO$_3$)$_2$); C, 26.02%; H, 3.02%; N, 16.34%; measured values; C, 25.92%; H, 3.21%; N, 16.18%.

Example 69

Synthesis of [W$^I$(iMP)(H$_2$O)](NO$_3$) {[46](NO$_3$)} (Step 1)

The pH of an aqueous solution of the [45](NO$_3$)$_2$ (0.85 mmol) obtained in Example 68 was adjusted to pH 6 using a 0.01 M aqueous nitric acid solution followed by introducing hydrogen (1 atm) into the aqueous solution at 25° C. for 24 hours and allowing to react to obtain [46](NO$_3$).
Elementary analysis: theoretical values ([46](NO$_3$)); C, 31.03%; H, 3.00%; N, 16.70%; measured values; C, 31.15%; H, 3.13%; N, 16.64%.

Example 70

Synthesis of [W$^{II}_2$(iMP)$_2$(H$_2$O)$_4$](NO$_3$)$_4$ {[47](NO$_3$)$_4$} (Step 2)

Sodium nitrate (0.66 mmol) was added to a suspended aqueous solution of the [46](NO$_3$) (0.65 mmol) obtained in Example 69 followed by introducing oxygen (1 atm) for 3 hours at 25° C., passing the resulting solution through Sephadex and removing the solvent under reduced pressure to obtain {47}(NO$_3$)$_4$.

Elementary analysis: theoretical values ([47](NO$_3$)$_4$); C, 26.77%; H, 2.94%; N, 16.81%; measured values; C, 26.61%; H, 2.82%; N, 16.68%.

Example 71

Synthesis of [W$^{III}_2$(iMP)$_2$(H$_2$O)$_4$(μ-η$^1$:η$^1$-O$_2$)](NO$_3$)$_4$ {[48](NO$_3$)$_4$} (Step 3)

Oxygen (1 atm) was passed through an aqueous solution of the {[47](NO$_3$)$_4$} (0.32 mmol) obtained in Example 70 for 3 hours at 25° C. followed by removing the solvent under reduced pressure to obtain [48](NO$_3$)$_4$.
Elementary analysis: theoretical values ([48](NO$_3$)$_4$); C, 26.06%; H, 2.86%; N, 16.36%; measured values; C, 26.21%; H, 3.01%; N, 16.12%.

Example 72

Release of Hydrogen Peroxide (Step 4) and Detection

Nitric acid was added to an aqueous solution of the [48](NO$_3$)$_4$ (0.31 mmol) obtained in Example 71 at 25° C. followed by reacting for 3 hours and releasing hydrogen peroxide. Quantitative determination was carried out using a titanium complex and the yield of hydrogen peroxide was 1%.

Example 73

Synthesis of [Re$^{III}$(iMP)Cl$_3$]

Re$^{III}$Cl$_3$ (2.0 mmol) and iMP (2.1 mmol) were heated to reflux in ethanol to obtain [Re$^{III}$(iMP)Cl$_3$] (Re$^{III}$Cl$_3$ is a commercially available product (rhenium trichloride)).
Elementary analysis: theoretical values ([Re$^{III}$(iMP)Cl$_3$]); C, 29.36%; H, 2.46%; N, 13.17%; measured values; C, 29.45%; H, 2.57%; N, 13.29%.

Example 74

Synthesis of [Re$^{III}$(iMP)(OH)(H$_2$O)$_2$](NO$_3$)$_2$ {[49](NO$_3$)$_2$}

AgNO$_3$ (3.0 mmol) was added to the [Re$^{III}$(iMP)Cl$_3$] (1.0 mmol) obtained in Example 73 in water followed by refluxing for 12 hours at 100° C. and precipitation of AgCl. AgCl was removed by filtering the reaction solution followed by removing the water from the filtrate under reduced pressure to obtain [49](NO$_3$)$_2$.
Elementary analysis: theoretical values ([49](NO$_3$)$_2$); C, 25.91%; H, 3.01%; N, 16.27%; measured values; C, 25.99%; H, 3.23%; N, 16.06%.

Example 75

Synthesis of [Re$^I$(iMP)(H$_2$O)](NO$_3$) {[50](NO$_3$)} (Step 1)

The pH of an aqueous solution of the [49](NO$_3$)$_2$ (0.81 mmol) obtained in Example 74 was adjusted to pH 6 using a 0.01 M aqueous nitric acid solution followed by introducing hydrogen (1 atm) into the aqueous solution at 25° C. for 24 hours to obtain [50](NO$_3$).

Example 76

Synthesis of [Re$^{II}_2$(iMP)$_2$(H$_2$O)$_4$](NO$_3$)$_4$ {[51](NO$_3$)$_4$} (Step 2)

Sodium nitrate (0.60 mmol) was added to a suspended aqueous solution of the [50](NO$_3$) (0.59 mmol) obtained in Example 75 followed by introducing oxygen (1 atm) for 3 hours at 25° C., passing the resulting solution through Sephadex and removing the solvent under reduced pressure to obtain [51](NO$_3$)$_4$.

Elementary analysis: theoretical values ([51](NO$_3$)$_4$); C, 26.67%; H, 2.93%; N, 16.75%; measured values; C, 26.53%; H, 2.75%; N, 16.58%.

Example 77

Synthesis of [Re$^{III}_2$(iMP)$_2$(H$_2$O)$_4$(μ-η$^1$:η$^1$-O$_2$)](NO$_3$)$_4$ {[52](NO$_3$)$_4$} (Step 3)

Oxygen (1 atm) was passed through an aqueous solution of the [51](NO$_3$)$_4$ (0.29 mmol) obtained in Example 76 for 3 hours at 25° C. followed by removing the solvent under reduced pressure to obtain [52](NO$_3$)$_4$.

Elementary analysis: theoretical values ([52](NO$_3$)$_4$); C, 25.96%; H, 2.85%; N, 16.30%; measured values; C, 25.78%; H, 3.05%; N, 16.14%.

Example 78

Release of Hydrogen Peroxide (Step 4) and Detection

Nitric acid was added to an aqueous solution of the [52](NO$_3$)$_4$ (0.28 mmol) obtained in Example 77 at 25° C. followed by reacting for 3 hours and releasing hydrogen peroxide. Quantitative determination was carried out using a titanium complex and the yield of hydrogen peroxide was 1%.

Example 79

Synthesis of [Os$^{III}$(iMP)Cl$_3$]

Os$^{III}$Cl$_3$ (2.0 mmol) and iMP (2.1 mmol) were heated to reflux in ethanol to obtain [Os$^{III}$(iMP)Cl$_3$] (Os$^{III}$Cl$_3$ is a commercially available product (osmium trichloride)).

Elementary analysis: theoretical values ([Os$^{III}$(iMP)Cl$_3$]); C, 29.14%; H, 2.45%; N, 13.07%; measured values; C, 29.35%; H, 2.42%; N, 13.01%.

Example 80

Synthesis of [Os$^{III}$(iMP)(OH)(H$_2$O)$_2$](NO$_3$)$_2$ {[53](NO$_3$)$_2$}

AgNO$_3$ (3.0 mmol) was added to the [Os$^{III}$(iMP)Cl$_3$] (1.0 mmol) obtained in Example 79 in water followed by refluxing for 12 hours at 100° C. and precipitation of AgCl. AgCl was removed by filtering the reaction solution followed by removing the water from the filtrate under reduced pressure to obtain [53](NO$_3$)$_2$.

Elementary analysis: theoretical values ([53](NO$_3$)$_2$); C, 25.74%; H, 2.99%; N, 16.16%; measured values; C, 25.78%; H, 3.05%; N, 15.98%.

Example 81

Synthesis of [Os$^{I}$(iMP)(H$_2$O)](NO$_3$) {[54](NO$_3$)} (Step 1)

The pH of an aqueous solution of the [53](NO$_3$)$_2$ (0.84 mmol) obtained in Example 80 was adjusted to pH 6 using a 0.01 M aqueous nitric acid solution followed by introducing hydrogen (1 atm) into the aqueous solution at 25° C. for 24 hours and allowing to react to obtain [54](NO$_3$).

Elementary analysis: theoretical values ([54](NO$_3$)); C, 30.64%; H, 2.97%; N, 16.49%; measured values; C, 30.54%; H, 2.89%; N, 16.35%.

Example 82

Synthesis of [Os$^{II}_2$(iMP)$_2$(H$_2$O)$_4$](NO$_3$)$_4$ {[55](NO$_3$)$_4$} (Step 2)

Sodium nitrate (0.69 mmol) was added to a suspended aqueous solution of the [54](NO$_3$) (0.68 mmol) obtained in Example 81 followed by introducing oxygen (1 atm) for 3 hours at 25° C., passing the resulting solution through Sephadex and removing the solvent under reduced pressure to obtain [55](NO$_3$)$_4$.

Elementary analysis: theoretical values ([55](NO$_3$)$_4$); C, 26.48%; H, 2.91%; N, 16.63%; measured values; C, 26.35%; H, 2.83%; N, 16.48%.

Example 83

Synthesis of [Os$^{III}_2$(iMP)$_2$(H$_2$O)$_4$(μ-η$^1$:η$^1$-O$_2$)](NO$_3$)$_4$ {[56](NO$_3$)$_4$} (Step 3)

Oxygen (1 atm) was passed through an aqueous solution of the [55](NO$_3$)$_4$ (0.34 mmol) obtained in Example 82 for 3 hours at 25° C. followed by removing the solvent under reduced pressure to obtain [56](NO$_3$)$_4$.

Elementary analysis: theoretical values ([56](NO$_3$)$_4$); C, 25.78%; H, 2.83%; N, 16.19%; measured values; C, 25.56%; H, 3.00%; N, 16.02%.

Example 84

Release of Hydrogen Peroxide (Step 4) and Detection

Nitric acid was added to an aqueous solution of the [56](NO$_3$)$_4$ (0.33 mmol) obtained in Example 83 at 25° C. followed by reacting for 3 hours and releasing hydrogen peroxide. Quantitative determination was carried out using a titanium complex and the yield of hydrogen peroxide was 1%.

Example 85

Synthesis of [Ir$^{III}$(iMP)Cl$_3$]

Ir$^{III}$Cl$_3$.3H$_2$O (2.0 mmol) and iMP (2.1 mmol) were heated to reflux in ethanol to obtain [Ir$^{III}$(iMP)Cl$_3$] (Ir$^{III}$Cl$_3$ is a commercially available product (iridium trichloride)).

Elementary analysis: theoretical values ([Ir$^{III}$(iMP)Cl$_3$]); C, 29.03%; H, 2.44%; (N, 13.02%; measured values; C, 29.29%; H, 2.55%; N, 13.12%.

Example 86

Synthesis of [Ir$^{III}$(iMP)(OH)(H$_2$O)$_2$](NO$_3$)$_2$ {[57](NO$_3$)$_2$}

AgNO$_3$ (3.0 mmol) was added to the [Ir$^{III}$(iMP)Cl$_3$] (1.0 mmol) obtained in Example 85 in water followed by refluxing for 12 hours at 100° C. and precipitation of AgCl. AgCl was removed by filtering the reaction solution followed by removing the water from the filtrate under reduced pressure to obtain [57](NO$_3$)$_2$.

Elementary analysis: theoretical values ([57](NO$_3$)$_2$); C, 25.66%; H, 2.98%; N, 16.11%; measured values; C, 25.77%; H, 3.13%; N, 16.24%.

Example 87

Synthesis of [Ir$^I$(iMP)(H$_2$O)](NO$_3$) {[58](NO$_3$)} (Step 1)

The pH of an aqueous solution of the [57](NO$_3$)$_2$ (0.80 mmol) obtained in Example 86 was adjusted to pH 6 using a 0.01 M aqueous nitric acid solution followed by introducing hydrogen (1 atm) into the aqueous solution at 25° C. for 24 hours and allowing to react to obtain [58](NO$_3$).

Elementary analysis: theoretical values ([58](NO$_3$)); C, 30.52%; H, 2.96%; N, 16.43%; measured values; C, 30.42%; H, 3.16%; N, 16.29%.

Example 88

Synthesis of [Ir$^{II}_2$(iMP)$_2$(H$_2$O)$_4$](NO$_3$)$_4$ {[59](NO$_3$)$_4$} (Step 2)

Sodium nitrate (0.59 mmol) was added to a suspended aqueous solution of the [58](NO$_3$) (0.58 mmol) obtained in Example 87 followed by introducing oxygen (1 atm) for 3 hours at 25° C., passing the resulting solution through Sephadex and removing the solvent under reduced pressure to obtain [59](NO$_3$)$_4$.

Elementary analysis: theoretical values ([59](NO$_3$)$_4$); C, 26.48%; H, 2.91%; N, 16.63%; measured values; C, 26.35%; H, 2.83%; N, 16.48%.

Example 89

Synthesis of [Ir$^{III}_2$(iMP)$_2$(H$_2$O)$_4$(μ-η$^1$:η$^1$-O$_2$)(NO$_3$)$_4$ {[60](NO$_3$)$_4$} (Step 3)

Oxygen (1 atm) was passed through an aqueous solution of the [59](NO$_3$)$_4$ (0.29 mmol) obtained in Example 88 for 3 hours at 25° C. followed by removing the solvent under reduced pressure to obtain [60](NO$_3$)$_4$.

Elementary analysis: theoretical values ([60](NO$_3$)$_4$); C, 25.70%; H, 2.82%; N, 16.14%; measured values; C, 25.91%; H, 2.90%; N, 15.97%.

Example 90

Release of Hydrogen Peroxide (Step 4) and Detection

Nitric acid was added to an aqueous solution of the [60](NO$_3$)$_4$ (0.28 mmol) obtained in Example 89 at 25° C. followed by reacting for 3 hours and releasing hydrogen peroxide. Quantitative determination was carried out using a titanium complex and the yield of hydrogen peroxide was 1%.

Example 91

Synthesis of [Pt$^{II}$(iMP)Cl$_2$]

Pt$^{II}$Cl$_2$ (2.0 mmol) and iMP (2.1 mmol) were heated to reflux in ethanol to obtain [Pt$^{II}$(iMP)Cl$_2$] (Pt$^{II}$Cl$_2$ is a commercially available product (platinum dichloride)).

Elementary analysis: theoretical values ([Pt$^{II}$(iMP)Cl$_2$]); C, 30.90%; H, 2.59%; N, 13.86%; measured values; C, 31.02%; H, 2.49%; N, 13.76%.

Example 92

Synthesis of [Pt$^{II}$(iMP)(OH)(H$_2$O)$_2$](NO$_3$) {[61](NO$_3$)}

AgNO$_3$ (2.0 mmol) was added to the [Pt$^{II}$(iMP)Cl$_2$] (1.0 mmol) obtained in Example 91 in water followed by refluxing for 12 hours at 100° C. and precipitation of AgCl. AgCl was removed by filtering the reaction solution followed by removing the water from the filtrate under reduced pressure to obtain [61](NO$_3$).

Elementary analysis: theoretical values ([61](NO$_3$)); C, 28.42%; H, 3.30%; N, 15.30%; measured values; C, 28.53%; H, 3.44%; N, 15.43%.

Example 93

Synthesis of [Pt$^0$(iMP)(H$_2$O)] {[62]} (Step 1)

The pH of an aqueous solution of the [61](NO$_3$) (0.86 mmol) obtained in Example 92 was adjusted to pH 6 using a 0.01 M aqueous nitric acid solution followed by introducing hydrogen (1 atm) into the aqueous solution at 25° C. for 24 hours and allowing to react to obtain [62].

Elementary analysis: theoretical values ([62]); C, 34.52%; H, 3.34%; N, 15.48%; measured values; C, 34.48%; H, 3.47%; N, 15.23%.

Example 94

Synthesis of [Pt$^I_2$(iMP)$_2$(H$_2$O)$_4$](NO$_3$)$_2$ {[63](NO$_3$)$_2$} (Step 2)

Sodium nitrate (0.61 mmol) was added to a suspended aqueous solution of the [62] (0.60 mmol) obtained in Example 93 followed by introducing oxygen (1 atm) for 3 hours at 25° C., passing the resulting solution through Sephadex and removing the solvent under reduced pressure to obtain [63](NO$_3$)$_2$.

Elementary analysis: theoretical values ([63](NO$_3$)$_2$); C, 29.33%; H, 3.22%; N, 15.79%; measured values; C, 26.13%; H, 2.68%; N, 16.31%.

Example 95

Synthesis of [Pt$^{II}_2$(iMP)$_2$(H$_2$O)$_4$(μ-η$^1$:η$^1$-O$_2$)(NO$_3$)$_2$ {[64](NO$_3$)$_2$} (Step 3)

Oxygen (1 atm) was passed through an aqueous solution of the [63](NO$_3$)$_2$ (0.30 mmol) obtained in Example 94 for 3 hours at 25° C. followed by removing the solvent under reduced pressure to obtain [64](NO$_3$)$_2$.

Elementary analysis: theoretical values ([64](NO$_3$)$_2$); C, 28.47%; H, 3.12%; N, 15.32%; measured values; C, 28.43%; H, 2.93%; N, 15.43%.

Example 96

Release of Hydrogen Peroxide (Step 4) and Detection

Nitric acid was added to an aqueous solution of the [64](NO$_3$)$_2$ (0.29 mmol) obtained in Example 95 at 25° C. followed by reacting for 3 hours and releasing hydrogen peroxide. Quantitative determination was carried out using a titanium complex and the yield of hydrogen peroxide was 1%.

Example 97

Synthesis of [Au$^{III}$(iMP)Cl$_3$]

Au$^{III}$Cl$_3$ (2.0 mmol) and iMP (2.1 mmol) were heated to reflux in ethanol to obtain [Au$^{III}$(iMP)Cl$_3$](Au$^{III}$Cl$_3$ is a commercially available product (gold trichloride)).

Elementary analysis: theoretical values ([Au$^{III}$(iMP)Cl$_3$]): C, 28.78%; H, 2.41%; N, 12.91%; measured values: C, 28.97%; H, 2.51%; N, 12.77%.

Example 98

Synthesis of [Au$^{III}$(iMP)(OH)(H$_2$O)$_2$](NO$_3$)$_2$ {[65](NO$_3$)$_2$}

AgNO$_3$ (3.0 mmol) was added to the [Au$^{III}$(iMP)Cl$_3$] (1.0 mmol) obtained in Example 97 in water followed by refluxing for 12 hours at 100° C. and precipitation of AgCl. AgCl was removed by filtering the reaction solution followed by removing the water from the filtrate under reduced pressure to obtain [65](NO$_3$)$_2$.

Elementary analysis: theoretical values ([65](NO$_3$)$_2$); C, 25.46%; H, 2.96%; N, 15.99%; measured values; C, 25.26%; H, 3.17%; N, 16.01%.

Example 99

Synthesis of [Au$^I$(iMP)(H$_2$O)](NO$_3$) {[66](NO$_3$)} (Step 1)

The pH of an aqueous solution of the [65](NO$_3$)$_2$ (0.84 mmol) obtained in Example 98 was adjusted to pH 6 using a 0.01 M aqueous nitric acid solution followed by introducing hydrogen (1 atm) into the aqueous solution at 25° C. for 24 hours and allowing to react to obtain [66](NO$_3$).

Elementary analysis: theoretical values ([66](NO$_3$)); C, 30.24%; H, 2.93%; N, 16.28%; measured values; C, 30.11%; H, 2.82%; N, 16.03%.

Example 100

Synthesis of [Au$^{II}_2$(iMP)$_2$(H$_2$O)$_4$](NO$_3$)$_4$ {[67](NO$_3$)$_4$} (Step 2)

Sodium nitrate (0.58 mmol) was added to a suspended aqueous solution of the [66](NO$_3$) (0.57 mmol) obtained in Example 99 followed by introducing oxygen (1 atm) for 3 hours at 25° C., passing the resulting solution through Sephadex and removing the solvent under reduced pressure to obtain [67](NO$_3$)$_4$.

Elementary analysis: theoretical values ([67](NO$_3$)$_4$); C, 26.19%; H, 2.87%; N, 16.44%; measured values; C, 26.01%; H, 2.91%; N, 16.57%.

Example 101

Synthesis of [Au$^{III}_2$(iMP)$_2$(H$_2$O)$_4$($\mu$-$\eta^1$:$\eta^1$-O$_2$)(NO$_3$)$_4$ {[68](NO$_3$)$_4$} (Step 3)

Oxygen (1 atm) was passed through an aqueous solution of the [67](NO$_3$)$_4$ (0.28 mmol) obtained in Example 100 for 3 hours at 25° C. followed by removing the solvent under reduced pressure to obtain [68](NO$_3$)$_4$.

Elementary analysis: theoretical values ([68](NO$_3$)$_4$); C, 25.50%; H, 2.80%; N, 16.01%; measured values; C, 25.64%; H, 2.73%; N, 15.91%.

Example 102

Release of Hydrogen Peroxide (Step 4) and Detection

Nitric acid was added to an aqueous solution of the [68](NO$_3$)$_4$ (0.27 mmol) obtained in Example 101 at 25° C. followed by reacting for 3 hours and releasing hydrogen peroxide. Quantitative determination was carried out using a titanium complex and the yield of hydrogen peroxide was 1%.

The invention claimed is:

1. A metal complex represented by a formula (1):

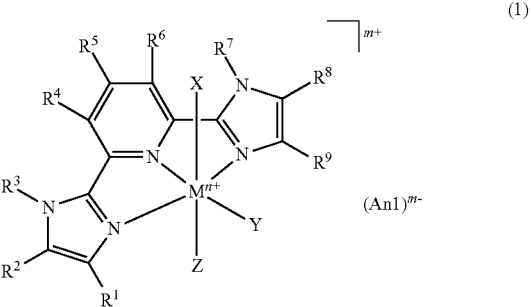

wherein M represents chromium, manganese, iron, cobalt, nickel, copper, molybdenum, ruthenium, rhodium, palladium, silver, tungsten, rhenium, osmium, iridium, platinum or gold, n+ represents a charge of M, $R^1$, $R^2$, $R^4$, $R^5$, $R^6$, $R^8$ and $R^9$ represents hydrogen atoms, $R^3$ and $R^7$ represent methyl groups, one of X, Y and Z represents OH$^-$, the remaining two represents H$_2$O, m+ represents +1, An1 represents a nitrate ion, and m− represents −1 the charge of An1.

2. A method for producing hydrogen peroxide, comprising: forming hydrogen peroxide from hydrogen and oxygen in the presence of the metal complex according to claim 1.

* * * * *